(12) United States Patent
Huang et al.

(10) Patent No.: US 8,283,439 B2
(45) Date of Patent: Oct. 9, 2012

(54) **RECOMBINANT FRAGMENTS AND SYNTHETIC PEPTIDES OF 17-KDA POLYPEPTIDE USEFUL IN DETECTING *BARTONELLA HENSELAE***

(75) Inventors: Lisa P. Huang, Princeton, NJ (US); John G. Hoey, Elmer, NJ (US); Martin E. Adelson, Belle Mead, NJ (US); Eli Mordechai, Robbinsville, NJ (US)

(73) Assignee: Medical Diagnostic Laboratories L.L.C., Hamilton, NJ (US)

( * ) Notice: Subject to any disclaimer, the term of this patent is extended or adjusted under 35 U.S.C. 154(b) by 0 days.

(21) Appl. No.: 12/462,602

(22) Filed: Aug. 6, 2009

(65) Prior Publication Data

US 2012/0058495 A1 Mar. 8, 2012

Related U.S. Application Data

(60) Provisional application No. 61/189,802, filed on Aug. 22, 2008, provisional application No. 61/215,420, filed on May 5, 2009.

(51) Int. Cl.
*C07K 14/195* (2006.01)
*G01N 33/53* (2006.01)

(52) U.S. Cl. .......... 530/300; 435/7.92; 435/810

(58) Field of Classification Search .......... None
See application file for complete search history.

(56) References Cited

U.S. PATENT DOCUMENTS

| | | | |
|---|---|---|---|
| 5,736,347 | A | 4/1998 | Anderson |
| 6,406,887 | B1 * | 6/2002 | Anderson et al. ............ 435/69.3 |
| 7,727,711 | B2 | 6/2010 | McCool |
| 2003/0235876 | A1 | 12/2003 | Bethke |
| 2010/0209936 | A1 | 8/2010 | Hoey |

OTHER PUBLICATIONS

Adelson, Martin E., et al., Journal of Clinical Microbiology, vol. 42, No. 6, 2004, pp. 2799-2801.
Agan, Brian K., and Dolan, Matthew J., Clin. Lab. Med. vol. 22, 2002, pp. 937-962.
Amerein, M. P., et al., Clinical and Diagnostic Laboratory Immunology, vol. 3, No. 2, 1996, pp. 200-204.
Anderson, Burt, et al., Journal of Clinical Microbiology, vol. 33, No. 9, 1995, pp. 2358-2365.
Arvand, Mardjan, et al., Clinical Infectious Diseases, vol. 26, 1998, pp. 1296-1299.
Asharaf, Mohammed and Letha, S., Indian Journal of Pediatrics, vol. 69, No. 11, 2002, pp. 1003-1005.
Bergmans, A. M. C., et al., Journal of Clinical Microbiology, vol. 35, No. 8, 1997, pp. 1931-1937.
Birtles, Richard J., et al., The New England Journal of Medicine, vol. 325, No. 20, 1991, pp. 1447-1448.
Branley, James, et al., Pathology, vol. 28, 1996, pp. 262-265.
Eskow, Eugene, et al, Arch. Neurol., vol. 58, 2001, pp. 1357-1363.
Fournier, Pierre-Edouard, et al., Clinical and Diagnostic Laboratory Immunology, vol. 9, No. 4, 2002, pp. 795-801.
La Scola, Bernard and Raoult, Didier, Journal of Clinical Microbiology, vol. 37, No. 6, 1999, pp. 1899-1905.
Margileth, Andrew M. and Baehren, David F., Clinical Infectious Diseases, vol. 27, 1998, pp. 353-357.
Sander, A., et al., Eur. J. Clin. Microbiol. Infect. Dis., vol. 20, 2001, pp. 392-401.
Shamaei-Tousi, Alireza, et al., Journal of Bacteriology, vol. 186, No. 14, 2004, pp. 4796-4801.

\* cited by examiner

*Primary Examiner* — Padma Baskar
(74) *Attorney, Agent, or Firm* — Siu K. Lo, Esq.

(57) ABSTRACT

The present disclosure describes recombinant and synthetic polypeptides of *Bartonella henselae* and related methods and kits for the detection of antibodies specific for *Bartonella henselae*. The 17-kDa polypeptides, methods and kits are useful in the detection of recent and/or ongoing infections with *Bartonella henselae*, which can be useful in the diagnosis of Cat Scratch Disease (CSD).

10 Claims, 38 Drawing Sheets

Figure 1

**17-kDa Gene Sequence (*Bartonella henselae*) (SEQ ID NO: 1)**

| | | | | |
|---|---|---|---|---|
| ATGAAAAAAT | ATAGCTTAGT | CACATTGTTA | TCTTTATTTT | 40 |
| GCATCTCTCA | TGCAAAAGCA | CAAACAGCAA | CCCTTACTGA | 80 |
| TGAATATTAT | AAAAAAGCCT | TAGAAAACAC | GCAAAAATTA | 120 |
| GACGTTGCAA | AATCACAAAC | AGCTGAGTCT | ATTTATGAAT | 160 |
| CTGCAACACA | AACTGCAAAC | AAAATTAAGG | ACATAAACAA | 200 |
| TCAACTTGCA | AATCTTAAAG | CAGATACAAA | GACTAAACCT | 240 |
| GAACAATTGC | AAGCCCTGCA | AATAGAGCTG | ACTCTTCTCC | 280 |
| AGGCACAGCT | GCAAGCGGAT | ACTTTAAAAA | TCCAGTCTCT | 320 |
| TGCTATGATT | CAAGCAAAAG | ATACGAAAAC | AAAAGAAGAA | 360 |
| TTGCGTGAAG | AGCAAACACA | AAAAAAGCAT | GAAGATCTTC | 400 |
| AAAAACAATT | AAAAGAAAAA | CTTGAGAAAT | CTGATGTCCG | 440 |
| ACTTTAG | | | | 447 |

**17-kDa Protein Sequence (*Bartonella henselae*) of the Present Invention (SEQ ID NO: 2)**

| | | | | |
|---|---|---|---|---|
| MKKYSLVTLL | SLFCISHAKA | QTATLTDEYY | KKALENTQKL | 40 |
| DVAKSQTAES | IYESATQTAN | KIKDINNQLA | NLKADTKTKP | 80 |
| EQLQALQIEL | TLLQAQLQAD | TLKIQSLAMI | QAKDTKTKEE | 120 |
| LREEQTQKKH | EDLQKQLKEK | LEKSDVQL | | 148 |

Figure 4

**17-kDa Fragment 1 Gene Sequence (*Bartonella henselae*) (SEQ ID NO: 3)**

```
TTTTGCATCT CTCATGCAAA AGCACAAACA GCAACCCTTA   40
CTGATGAATA TTATAAAAAA GCCTTAGAAA ACACGCAAAA   80
ATTAGACGTT GCAAAATCAC AAACAGCTGA GTCTATTTAT  120
GAATCTGCAA CACAAACTGC AAACAAAATT AAGGACATAA  160
ACAATCAACT TGCAAATCTT AAAGCA                 186
```

**17-kDa Fragment 1 Protein Sequence (*Bartonella henselae*) (SEQ ID NO: 4)**

```
FCISHAKAQT ATLTDEYYKK ALENTQKLDV AKSQTAESIY   40
ESATQTANKI KDINNQLANL KA                     62
```

Figure 7

**17-kDa Fragment 2 Gene Sequence (*Bartonella henselae*) (SEQ ID NO: 5)**

| | | | | |
|---|---|---|---|---|
| AAGGACATAA | ACAATCAACT | TGCAAATCTT | AAAGCAGATA | 40 |
| CAAAGACTAA | ACCTGAACAA | TTGCAAGCCC | TGCAAATAGA | 80 |
| GCTGACTCTT | CTCCAGGCAC | AGCTGCAAGC | GGATACTTTA | 120 |
| AAAATCCAGT | CTCTTGCTAT | GATTCAAGCA | AAAGATACGA | 160 |
| AAACAAAAGA | AGAATTGCGT | GAAGAGCAAA | CACAAAAAAA | 200 |
| GCATGAAGAT | CTT | | | 213 |

**17-kDa Fragment 2 Protein Sequence (*Bartonella henselae*) (SEQ ID NO: 6)**

| | | | | |
|---|---|---|---|---|
| KDINNQLANL | KADTKTKPEQ | LQALQIELTL | LQAQLQADTL | 40 |
| KIQSLAMIQA | KDTKTKEELR | EEQTQKKHED | L | 71 |

Figure 8

**17-kDa Fragment 4 Gene Sequence (*Bartonella henselae*) (SEQ ID NO: 7)**

```
GAACAATTGC AAGCCCTGCA AATAGAGCTG ACTCTTCTCC   40
AGGCACAGCT GCAAGCGGAT ACTTTAAAAA TCCAGTCTCT   80
TGCTATG                                       87
```

**17-kDa Fragment 4 Protein Sequence (*Bartonella henselae*) (SEQ ID NO: 8)**

```
EQLQALQIEL TLLQAQLQAD TLKIQSLAM               29
```

Figure 9

**17-kDa Fragment 3 Gene Sequence (*Bartonella henselae*) (SEQ ID NO: 9)**

```
AAGACTAAAC CTGAACAATT GCAAGCCCTG CAAATAGAGC    40
TGACTCTTCT CCAGGCACAG CTGCAAGCGG ATACTTTAAA    80
AATCCAGTCT CTTGCTATGA TTCAAGCAAA AGATACGAAA   120
ACAAAAGAAG AATTGCGTGA AGAGCAAACA CAAAAAAAGC   140
ATGAAGATCT TCAAAAACAA TTAAAAGAAA AACTTGAGAA   200
ATCTGATGTC CGACTT                             216
```

**17-kDa Fragment 3 Protein Sequence (*Bartonella henselae*) of Present Invention (SEQ ID NO: 10)**

```
KTKPEQLQAL QIELTLLQAQ LQADTLKIQS LAMIQAKDTK    40
TKEELREEQT QKKHEDLQKQ LKEKLEKSDV QL            72
```

1. BL21 (DE3) cell lysate without induction
2. BL21 (DE3) cell lysate over night induction
3. Cleared cell supernatant
4. Cell pellet 1. Lysate before column loading
2. Lysate after column loading
3. Wash-1
4. Wash-2
5. Elution-1
6. Elution-2
7. Elution-3
8. Elution-4
9. Elution-5
10. Elution-6
11. Elution-7

1. Lysate before column loading
2. Lysate after column loading
3. Bind wash -1
4. Bind wash -2
5. Wash -1
6. Wash -2
7. Elution -1
8. Elution -2
9. Elution -3
10. Elution -4
11. Elution -5
12. Elution -6

Figure 17
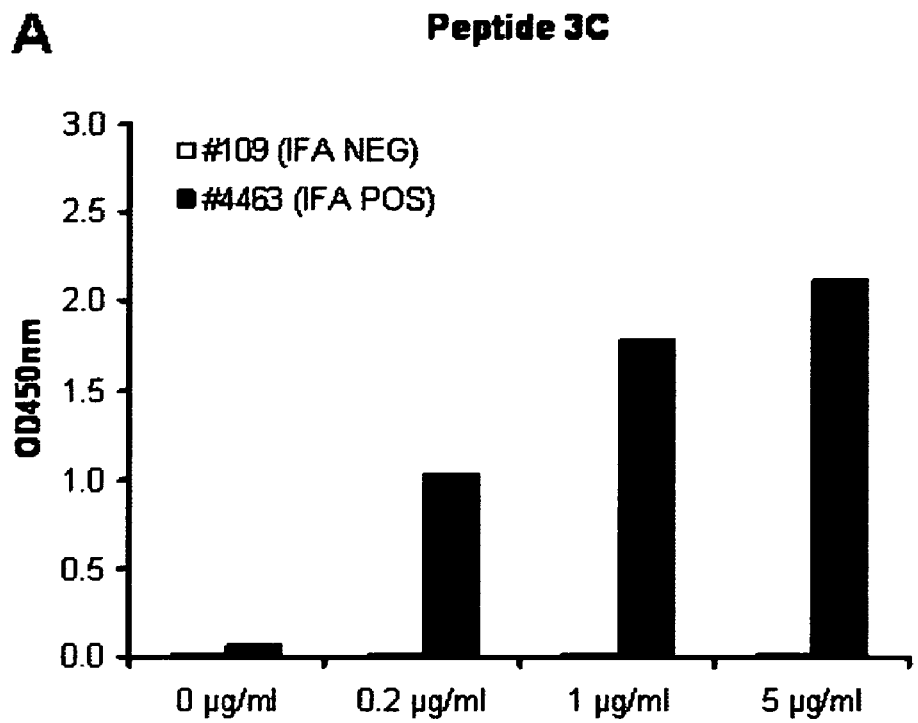
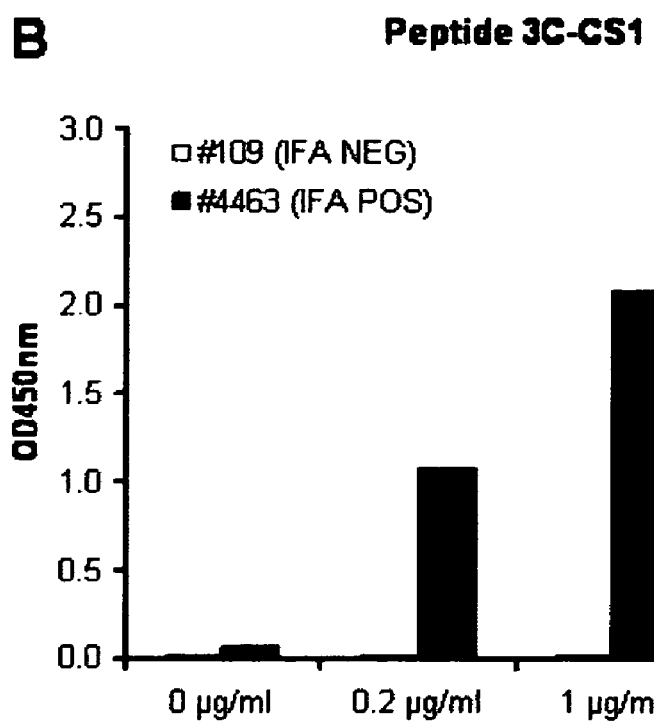

Figure 22

**17-kDa Fragment 3 Protein Sequence (*Bartonella henselae*) Published in NCBI (gi|49476013|ref|YP_034054.1|)**

```
KTKPE QLQAL QIELT LLQAQ LQADT LKIQS LAMIQ AKDTK        40
TKEEL REEQT QKKHE DLQKQ LKEKL EKSDV RL                 72
```

**17-kDa Fragment 3 Protein Sequence (*Bartonella henselae*) of the Present Invention (SEQ ID NO: 2)**

```
KTKPE QLQAL QIELT LLQAQ LQADT LKIQS LAMIQ AKDTK        40
TKEEL REEQT QKKHE DLQKQ LKEKL EKSDV QL                 72
```

Figure 23

**17-kDa Fragment 3 Protein Sequence (*Bartonella henselae*) of the Present Invention (SEQ ID NO: 2)**

```
KTKPE QLQAL QIELT LLQAQ LQADT LKIQS LAMIQ AKDTK      40
TKEEL REEQT QKKHE DLQKQ LKEKL EKSDV QL               72
```

Conservative Mutation E(13)D (SEQ ID NO: 42)

```
KTKPE QLQAL QIDLT LLQAQ LQADT LKIQS LAMIQ AKDTK      40
TKEEL REEQT QKKHE DLQKQ LKEKL EKSDV QL               72
```

Conservative Mutation L(16)V (SEQ ID NO: 43)

```
KTKPE QLQAL QIELT VLQAQ LQADT LKIQS LAMIQ AKDTK      40
TKEEL REEQT QKKHE DLQKQ LKEKL EKSDV QL               72
```

Deletion Mutation ΔQ(11) (SEQ ID NO: 44)

```
KTKPE QLQAL  IELT LLQAQ LQADT LKIQS LAMIQ AKDTK      39
TKEEL REEQT QKKHE DLQKQ LKEKL EKSDV QL               71
```

Insertion Mutation +V(17-18) (SEQ ID NO: 45)

```
KTKPE QLQAL QIELT LLVQAQ LQADT LKIQS LAMIQ AKDTK     41
TKEEL REEQT QKKHE DLQKQ LKEKL EKSDV QL               73
```

Figure 25

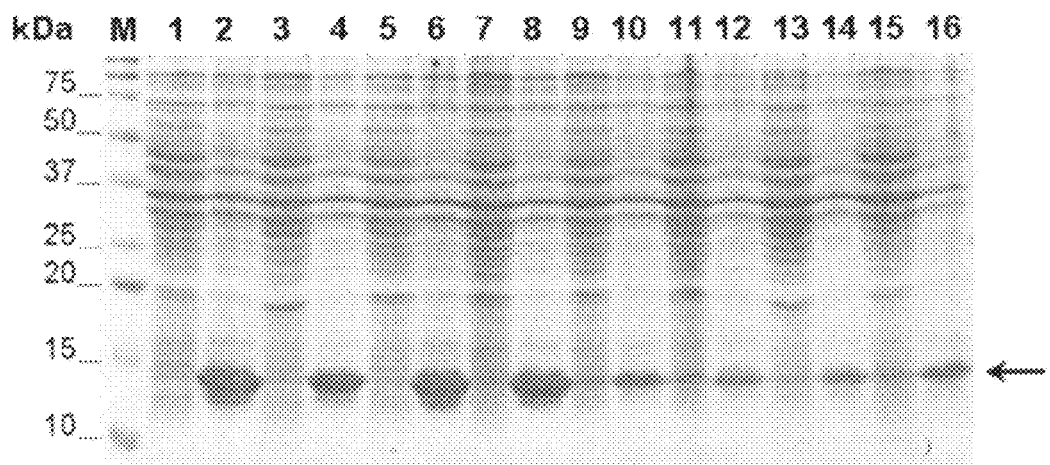

Overnight Induction of 17-kDa Fragment 3 Mutation Proteins

A

1. E(13)D clone #2A without induction
2. E(13)D clone #2A with induction
3. E(13)D clone #2B without induction
4. E(13)D clone #2B with induction
5. E(13)D clone #4A without induction
6. E(13)D clone #4A with induction
7. E(13)D clone #4B without induction
8. E(13)D clone #4B with induction
9. L(16)V clone #1A without induction
10. L(16)V clone #1A with induction
11. L(16)V clone #1B without induction
12. L(16)V clone #1B with induction
13. L(16)V clone #2A without induction
14. L(16)V clone #2A with induction
15. L(16)V clone #2B without induction
16. L(16)V clone #2B with induction M. Protein molecular weight marker Ni-NTA Purification of Recombinant 17-kDa Fragment 3 Conservative Mutation E(13)D 1. Lysate before column loading
2. Lysate after column loading
3-4 Wash with binding buffer
5-6 Wash with washing buffer
7-12 Elution
M. Protein molecular weight marker 1. Lysate before column loading
2. Lysate after column loading
3-4 Wash with binding buffer
5-6 Wash with washing buffer
7-12 Elution
M. Protein molecular weight marker Figure 33
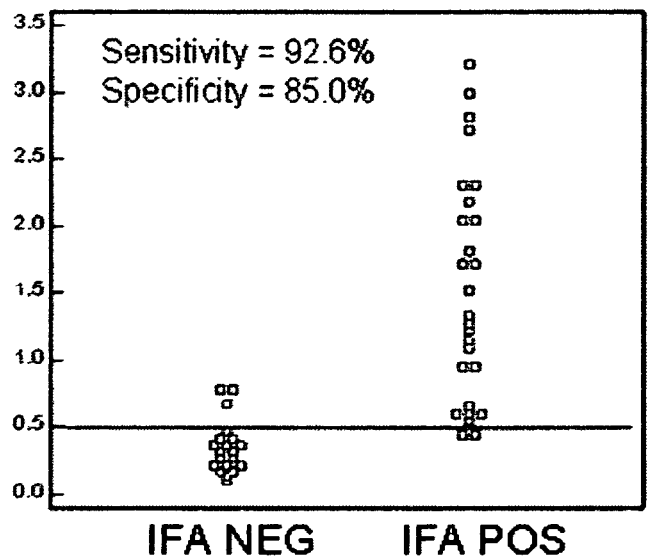
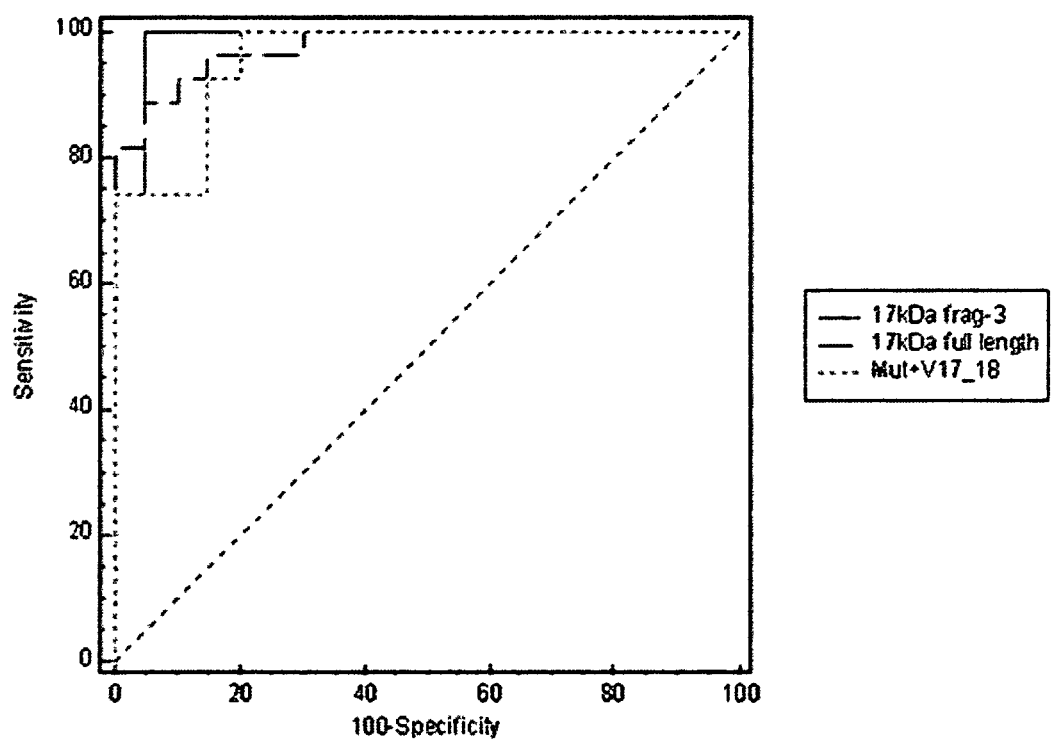

SEQUENCE LISTING

```
<160> NUMBER OF SEQ ID NOS: 45

<210> SEQ ID NO 1
<211> LENGTH: 447
<212> TYPE: DNA
<213> ORGANISM: Bartonella henselae

<400> SEQUENCE: 1
atgaaaaaat atagcttagt cacattgtta tctttatttt gcatctctca tgcaaaagca      60
caaacagcaa cccttactga tgaatattat aaaaagcct tagaaaacac gcaaaaatta      120
gacgttgcaa aatcacaaac agctgagtct atttatgaat ctgcaacaca aactgcaaac      180
aaaattaagg acataaacaa tcaacttgca aatcttaaag cagatacaaa gactaaacct      240
gaacaattgc aagccctgca aatagagctg actcttctcc aggcacagct gcaagcggat      300 acttttaaaaa tccagtctct tgctatgatt caagcaaaag atacgaaaac aaaagaagaa      360
```

```
ttgcgtgaag agcaaacaca aaaaaagcat gaagatcttc aaaaacaatt aaaagaaaaa    420
cttgagaaat ctgatgtcca actttag                                         447
```

<210> SEQ ID NO 2
<211> LENGTH: 148
<212> TYPE: PRT
<213> ORGANISM: Bartonella henselae

<400> SEQUENCE: 2

```
Met Lys Lys Tyr Ser Leu Val Thr Leu Leu Ser Leu Phe Cys Ile Ser
 1               5                  10                  15

His Ala Lys Ala Gln Thr Ala Thr Leu Thr Asp Glu Tyr Tyr Lys Lys
            20                  25                  30

Ala Leu Glu Asn Thr Gln Lys Leu Asp Val Ala Lys Ser Gln Thr Ala
        35                  40                  45

Glu Ser Ile Tyr Glu Ser Ala Thr Gln Thr Ala Asn Lys Ile Lys Asp
    50                  55                  60

Ile Asn Asn Gln Leu Ala Asn Leu Lys Ala Asp Thr Lys Thr Lys Pro
65                  70                  75                  80

Glu Gln Leu Gln Ala Leu Gln Ile Glu Leu Thr Leu Leu Gln Ala Gln
                85                  90                  95

Leu Gln Ala Asp Thr Leu Lys Ile Gln Ser Leu Ala Met Ile Gln Ala
            100                 105                 110

Lys Asp Thr Lys Thr Lys Glu Glu Leu Arg Glu Gln Thr Gln Lys
        115                 120                 125

Lys His Glu Asp Leu Gln Lys Gln Leu Lys Glu Lys Leu Glu Lys Ser
    130                 135                 140

Asp Val Gln Leu
145
```

<210> SEQ ID NO 3
<211> LENGTH: 186
<212> TYPE: DNA
<213> ORGANISM: Bartonella henselae

<400> SEQUENCE: 3

```
ttttgcatct ctcatgcaaa agcacaaaca gcaacccta ctgatgaata ttataaaaaa     60
gccttagaaa acacgcaaaa attagacgtt gcaaaatcac aaacagctga gtctatttat   120
gaatctgcaa cacaaactgc aaacaaaatt aaggacataa acaatcaact tgcaaatctt   180
aaagca                                                              186
```

<210> SEQ ID NO 4
<211> LENGTH: 62
<212> TYPE: PRT
<213> ORGANISM: Bartonella henselae

<400> SEQUENCE: 4

```
Phe Cys Ile Ser His Ala Lys Ala Gln Thr Ala Thr Leu Thr Asp Glu
 1               5                  10                  15

Tyr Tyr Lys Lys Ala Leu Glu Asn Thr Gln Lys Leu Asp Val Ala Lys
            20                  25                  30

Ser Gln Thr Ala Glu Ser Ile Tyr Glu Ser Ala Thr Gln Thr Ala Asn
        35                  40                  45

Lys Ile Lys Asp Ile Asn Asn Gln Leu Ala Asn Leu Lys Ala
    50                  55                  60
```

```
<210> SEQ ID NO 5
<211> LENGTH: 213
<212> TYPE: DNA
<213> ORGANISM: Bartonella henselae

<400> SEQUENCE: 5
aaggacataa acaatcaact tgcaaatctt aaagcagata caaagactaa acctgaacaa      60
ttgcaagccc tgcaaataga gctgactctt ctccaggcac agctgcaagc ggatacttta     120
aaaatccagt ctcttgctat gattcaagca aaagatacga aaacaaaaga agaattgcgt     180
gaagagcaaa cacaaaaaaa gcatgaagat ctt                                  213

<210> SEQ ID NO 6
<211> LENGTH: 71
<212> TYPE: PRT
<213> ORGANISM: Bartonella henselae

<400> SEQUENCE: 6

Lys Asp Ile Asn Asn Gln Leu Ala Asn Leu Lys Ala Asp Thr Lys Thr
 1               5                  10                  15

Lys Pro Glu Gln Leu Gln Ala Leu Gln Ile Glu Leu Thr Leu Leu Gln
            20                  25                  30

Ala Gln Leu Gln Ala Asp Thr Leu Lys Ile Gln Ser Leu Ala Met Ile
        35                  40                  45

Gln Ala Lys Asp Thr Lys Thr Lys Glu Glu Leu Arg Glu Glu Gln Thr
    50                  55                  60

Gln Lys Lys His Glu Asp Leu
65                  70

<210> SEQ ID NO 7
<211> LENGTH: 87
<212> TYPE: DNA
<213> ORGANISM: Bartonella henselae

<400> SEQUENCE: 7
gaacaattgc aagccctgca aatagagctg actcttctcc aggcacagct gcaagcggat      60
actttaaaaa tccagtctct tgctatg                                         87

<210> SEQ ID NO 8
<211> LENGTH: 29
<212> TYPE: PRT
<213> ORGANISM: Bartonella henselae

<400> SEQUENCE: 8

Glu Gln Leu Gln Ala Leu Gln Ile Glu Leu Thr Leu Leu Gln Ala Gln
 1               5                  10                  15

Leu Gln Ala Asp Thr Leu Lys Ile Gln Ser Leu Ala Met
            20                  25

<210> SEQ ID NO 9
<211> LENGTH: 216
<212> TYPE: DNA
<213> ORGANISM: Bartonella henselae

<400> SEQUENCE: 9
aagactaaac ctgaacaatt gcaagccctg caaatagagc tgactcttct ccaggcacag      60
ctgcaagcgg atactttaaa aatccagtct cttgctatga ttcaagcaaa agatacgaaa     120
acaaaagaag aattgcgtga agagcaaaca caaaaaaagc atgaagatct tcaaaaacaa     180
ttaaaagaaa aacttgagaa atctgatgtc caactt                               216
```

```
<210> SEQ ID NO 10
<211> LENGTH: 72
<212> TYPE: PRT
<213> ORGANISM: Bartonella henselae

<400> SEQUENCE: 10

Lys Thr Lys Pro Glu Gln Leu Gln Ala Leu Gln Ile Glu Leu Thr Leu
 1               5                  10                  15

Leu Gln Ala Gln Leu Gln Ala Asp Thr Leu Lys Ile Gln Ser Leu Ala
            20                  25                  30

Met Ile Gln Ala Lys Asp Thr Lys Thr Lys Glu Glu Leu Arg Glu Glu
        35                  40                  45

Gln Thr Gln Lys Lys His Glu Asp Leu Gln Lys Gln Leu Lys Glu Lys
    50                  55                  60

Leu Glu Lys Ser Asp Val Gln Leu
65                  70

<210> SEQ ID NO 11
<211> LENGTH: 32
<212> TYPE: DNA
<213> ORGANISM: Bartonella henselae

<400> SEQUENCE: 11
gacgacgaca agatggctgc ctatatttca tc                                32

<210> SEQ ID NO 12
<211> LENGTH: 33
<212> TYPE: DNA
<213> ORGANISM: Bartonella henselae

<400> SEQUENCE: 12
gaggagaagc ccggtcttaa ttttgtttgc agt                               33

<210> SEQ ID NO 13
<211> LENGTH: 33
<212> TYPE: DNA
<213> ORGANISM: Bartonella henselae

<400> SEQUENCE: 13
gacgacgaca agatgacata aacaatcaac ttg                               33

<210> SEQ ID NO 14
<211> LENGTH: 32
<212> TYPE: DNA
<213> ORGANISM: Bartonella henselae

<400> SEQUENCE: 14
gaggagaagc ccggtgaaga tcttcatgct tt                                32

<210> SEQ ID NO 15
<211> LENGTH: 33
<212> TYPE: DNA
<213> ORGANISM: Bartonella henselae

<400> SEQUENCE: 15
gacgacgaca agatgactaa acctgaacaa ttg                               33

<210> SEQ ID NO 16
<211> LENGTH: 31
<212> TYPE: DNA
<213> ORGANISM: Bartonella henselae

<400> SEQUENCE: 16
```

```
gaggagaagc ccggtctaag tcggacatca g                           31
```

<210> SEQ ID NO 17
<211> LENGTH: 30
<212> TYPE: DNA
<213> ORGANISM: Bartonella henselae

<400> SEQUENCE: 17

```
gacgacgaca agatgaacaa ttgcaagccc                              30
```

<210> SEQ ID NO 18
<211> LENGTH: 31
<212> TYPE: DNA
<213> ORGANISM: Bartonella henselae

<400> SEQUENCE: 18

```
gaggagaagc ccggtcatag caagagactg g                            31
```

<210> SEQ ID NO 19
<211> LENGTH: 18
<212> TYPE: PRT
<213> ORGANISM: Bartonella henselae

<400> SEQUENCE: 19

Ile Ser His Ala Lys Ala Gln Thr Ala Thr Leu Thr Asp Glu Tyr Tyr
 1               5                  10                  15

Lys Lys

<210> SEQ ID NO 20
<211> LENGTH: 18
<212> TYPE: PRT
<213> ORGANISM: Bartonella henselae

<400> SEQUENCE: 20

Glu Gln Leu Gln Ala Leu Gln Ile Glu Leu Thr Leu Leu Gln Ala Gln
 1               5                  10                  15

Leu Gln

<210> SEQ ID NO 21
<211> LENGTH: 18
<212> TYPE: PRT
<213> ORGANISM: Bartonella henselae

<400> SEQUENCE: 21

Gln Ala Lys Asp Thr Lys Thr Lys Glu Glu Leu Arg Glu Glu Gln Thr
 1               5                  10                  15

Gln Lys

<210> SEQ ID NO 22
<211> LENGTH: 18
<212> TYPE: PRT
<213> ORGANISM: Bartonella henselae

<400> SEQUENCE: 22

Glu Asp Leu Gln Lys Gln Leu Lys Glu Lys Leu Glu Lys Ser Asp Val
 1               5                  10                  15

Arg Leu

<210> SEQ ID NO 23
<211> LENGTH: 16
<212> TYPE: PRT
<213> ORGANISM: Bartonella henselae

<400> SEQUENCE: 23

Glu Glu Gln Thr Gln Lys Lys His Glu Asp Leu Gln Lys Gln Leu Lys
1               5                   10                  15

<210> SEQ ID NO 24
<211> LENGTH: 18
<212> TYPE: PRT
<213> ORGANISM: Bartonella henselae

<400> SEQUENCE: 24

Asp Asp Leu Gln Lys Gln Leu Lys Glu Lys Leu Glu Lys Ser Asp Val
1               5                   10                  15

Arg Leu

<210> SEQ ID NO 25
<211> LENGTH: 18
<212> TYPE: PRT
<213> ORGANISM: Bartonella henselae

<400> SEQUENCE: 25

Glu Asp Ile Gln Lys Gln Leu Lys Glu Lys Leu Glu Lys Ser Asp Val
1               5                   10                  15

Arg Leu

<210> SEQ ID NO 26
<211> LENGTH: 18
<212> TYPE: PRT
<213> ORGANISM: Bartonella henselae

<400> SEQUENCE: 26

Glu Asp Leu Gln Lys Gln Val Lys Glu Lys Leu Glu Lys Ser Asp Val
1               5                   10                  15

Arg Leu

<210> SEQ ID NO 27
<211> LENGTH: 18
<212> TYPE: PRT
<213> ORGANISM: Bartonella henselae

<400> SEQUENCE: 27

Leu Lys Gln Asp Glu Gln Lys Leu Glu Lys Leu Glu Lys Ser Asp Val
1               5                   10                  15

Arg Leu

<210> SEQ ID NO 28
<211> LENGTH: 18
<212> TYPE: PRT
<213> ORGANISM: Bartonella henselae

<400> SEQUENCE: 28

Glu Asp Leu Gln Lys Gln Leu Lys Ser Asp Lys Glu Val Lys Leu Arg
1               5                   10                  15

Leu Glu

<210> SEQ ID NO 29
<211> LENGTH: 18
<212> TYPE: PRT
<213> ORGANISM: Bartonella henselae

<400> SEQUENCE: 29

Leu Lys Leu Glu Leu Glu Leu Val Gln Asp Ser Asp Lys Gln Glu Lys

Arg Lys

<210> SEQ ID NO 30
<211> LENGTH: 22
<212> TYPE: PRT
<213> ORGANISM: Bartonella henselae

<400> SEQUENCE: 30

Gln Lys Lys His Glu Asp Leu Gln Lys Gln Leu Lys Glu Lys Leu Glu
1               5                   10                  15

Lys Ser Asp Val Arg Leu
            20

<210> SEQ ID NO 31
<211> LENGTH: 25
<212> TYPE: PRT
<213> ORGANISM: Bartonella henselae

<400> SEQUENCE: 31

Glu Gln Thr Gln Lys Lys His Glu Asp Leu Gln Lys Gln Leu Lys Glu
1               5                   10                  15

Lys Leu Glu Lys Ser Asp Val Arg Leu
            20                  25

<210> SEQ ID NO 32
<211> LENGTH: 17
<212> TYPE: PRT
<213> ORGANISM: Bartonella henselae

<400> SEQUENCE: 32

Glu Asp Gln Lys Gln Leu Lys Glu Lys Leu Glu Lys Ser Asp Val Arg
1               5                   10                  15

Leu

<210> SEQ ID NO 33
<211> LENGTH: 10
<212> TYPE: PRT
<213> ORGANISM: Bartonella henselae

<400> SEQUENCE: 33

Glu Lys Leu Glu Lys Ser Asp Val Arg Leu
1               5                   10

<210> SEQ ID NO 34
<211> LENGTH: 32
<212> TYPE: DNA
<213> ORGANISM: Bartonella henselae

<400> SEQUENCE: 34
gcaagccctg caaatagacc tgactcttct cc                                       32

<210> SEQ ID NO 35
<211> LENGTH: 32
<212> TYPE: DNA
<213> ORGANISM: Bartonella henselae

<400> SEQUENCE: 35
ggagaagagt caggtctatt tgcagggctt gc                                       32

<210> SEQ ID NO 36
<211> LENGTH: 28
<212> TYPE: DNA

```
<213> ORGANISM: Bartonella henselae

<400> SEQUENCE: 36
gagctgactg ttctccaggc acagctgc                                          28

<210> SEQ ID NO 37
<211> LENGTH: 28
<212> TYPE: DNA
<213> ORGANISM: Bartonella henselae

<400> SEQUENCE: 37
gcagctgtgc ctggagaaca gtcagctc                                          28

<210> SEQ ID NO 38
<211> LENGTH: 29
<212> TYPE: DNA
<213> ORGANISM: Bartonella henselae

<400> SEQUENCE: 38
gcaagccctg atagagctga ctcttctcc                                         29

<210> SEQ ID NO 39
<211> LENGTH: 29
<212> TYPE: DNA
<213> ORGANISM: Bartonella henselae

<400> SEQUENCE: 39
ggagaagagt cagctctatc agggcttgc                                         29

<210> SEQ ID NO 40
<211> LENGTH: 28
<212> TYPE: DNA
<213> ORGANISM: Bartonella henselae

<400> SEQUENCE: 40
ctgactcttc tcgtccaggc acagctgc                                          28

<210> SEQ ID NO 41
<211> LENGTH: 28
<212> TYPE: DNA
<213> ORGANISM: Bartonella henselae

<400> SEQUENCE: 41
gcagctgtgc ctggacgaga agagtcag                                          28

<210> SEQ ID NO 42
<211> LENGTH: 72
<212> TYPE: PRT
<213> ORGANISM: Bartonella henselae

<400> SEQUENCE: 42

Lys Thr Lys Pro Glu Gln Leu Gln Ala Leu Gln Ile Asp Leu Thr Leu
 1               5                  10                  15

Leu Gln Ala Gln Leu Gln Ala Asp Thr Leu Lys Ile Gln Ser Leu Ala
            20                  25                  30

Met Ile Gln Ala Lys Asp Thr Lys Thr Lys Glu Glu Leu Arg Glu Glu
        35                  40                  45

Gln Thr Gln Lys Lys His Glu Asp Leu Gln Lys Gln Leu Lys Glu Lys
    50                  55                  60

Leu Glu Lys Ser Asp Val Gln Leu
65                  70
```

```
<210> SEQ ID NO 43
<211> LENGTH: 72
<212> TYPE: PRT
<213> ORGANISM: Bartonella henselae

<400> SEQUENCE: 43

Lys Thr Lys Pro Glu Gln Leu Gln Ala Leu Gln Ile Glu Leu Thr Val
1               5                   10                  15

Leu Gln Ala Gln Leu Gln Ala Asp Thr Leu Lys Ile Gln Ser Leu Ala
            20                  25                  30

Met Ile Gln Ala Lys Asp Thr Lys Thr Lys Glu Glu Leu Arg Glu Glu
        35                  40                  45

Gln Thr Gln Lys Lys His Glu Asp Leu Gln Lys Gln Leu Lys Glu Lys
    50                  55                  60

Leu Glu Lys Ser Asp Val Gln Leu
65                  70

<210> SEQ ID NO 44
<211> LENGTH: 71
<212> TYPE: PRT
<213> ORGANISM: Bartonella henselae

<400> SEQUENCE: 44

Lys Thr Lys Pro Glu Gln Leu Gln Ala Leu Ile Glu Leu Thr Leu Leu
1               5                   10                  15

Gln Ala Gln Leu Gln Ala Asp Thr Leu Lys Ile Gln Ser Leu Ala Met
            20                  25                  30

Ile Gln Ala Lys Asp Thr Lys Thr Lys Glu Glu Leu Arg Glu Glu Gln
        35                  40                  45

Thr Gln Lys Lys His Glu Asp Leu Gln Lys Gln Leu Lys Glu Lys Leu
    50                  55                  60

Glu Lys Ser Asp Val Gln Leu
65                  70

<210> SEQ ID NO 45
<211> LENGTH: 73
<212> TYPE: PRT
<213> ORGANISM: Bartonella henselae

<400> SEQUENCE: 45

Lys Thr Lys Pro Glu Gln Leu Gln Ala Leu Gln Ile Glu Leu Thr Leu
1               5                   10                  15

Leu Val Gln Ala Gln Leu Gln Ala Asp Thr Leu Lys Ile Gln Ser Leu
            20                  25                  30

Ala Met Ile Gln Ala Lys Asp Thr Lys Thr Lys Glu Glu Leu Arg Glu
        35                  40                  45

Glu Gln Thr Gln Lys Lys His Glu Asp Leu Gln Lys Gln Leu Lys Glu
    50                  55                  60

Lys Leu Glu Lys Ser Asp Val Gln Leu
65                  70
```

RECOMBINANT FRAGMENTS AND SYNTHETIC PEPTIDES OF 17-KDA POLYPEPTIDE USEFUL IN DETECTING BARTONELLA HENSELAE

CROSS REFERENCE TO RELATED APPLICATIONS

The present application claims the benefit under 35 U.S.C. §1.119(e) of priority to U.S. Provisional Application Nos. 61/189,802 filed Aug. 22, 2008 and 61/215,420 filed May 5, 2009, the entire disclosure of which is hereby incorporated by reference in its entirety.

FIELD OF THE INVENTION

The present invention relates generally to the field of diagnostic assays for the detection of infectious agents in animals, including humans. Particular embodiments disclosed herein encompass novel recombinant fragments and synthetic polypeptides of 17-kDa protein that can be employed in the detection of Bartonella henselae.

BACKGROUND OF THE INVENTION

Bartonella henselae is the etiologic agent of cat scratch disease (CSD) (Bass et al., 1997; Branley et al., 1996; Chomel, 2000) and can also cause bacillary angiomatosis (BA) in immunocompromised patients (Arvand et al., 1998; Asharaf and Letha, 2002; Birtles et al., 1991; Chomel, 1996). CSD is common in children and young adults who have had scratches or bites from infected domestic cats (Chomel, 2000) and is characterized by fever and regional lymphadenopathy. Normally, the disease self-resolves in about three (3) months. However, in immuno-compromised patients, Bartonella infection frequently manifests as a more severe and life-threatening illnesses, including BA, endocarditis, encephalopathy, and pulmonary disease (Margileth and Baehren, 1998; Regnery and Tappero, 1995). BA is characterized by cutaneous and subcutaneous vascular lesions in which the bacteria invade endothelial cells resulting in hemangiomas. BA was initially described in patients infected with human immunodeficiency virus and has been extended to include patients with proliferative vascular lesions affecting different organs such as bone, liver, and spleen (Regnery and Tappero, 1995).

Bartonella henselae is identified by molecular and serology detection (Eskow et al., 2001). Molecular identification of bacterial genes by PCR amplification is applicable only in a laboratory with the proper equipment, expertise, and quality control procedures. PCR is useful in detecting during early-stage infection where the bacterium is still present in the peripheral blood stream. Molecular detection by PCR is suggested for surgically excised infected heart valves, but is less sensitive for peripheral blood samples because of a low pathogen bioavailability.

Serology is currently the most common diagnostic test for the determination of Bartonella infection (Houpikian and Raoult, 2002, 2003; Sander et al., 2001). Bacterial isolation of this fastidious organism by culturing is difficult because of lengthy incubation periods resulting in low sensitivity, especially for patients receiving antibiotic therapy (Agan and Dolan, 2002; La Scola and Raoult, 1999).

Immunofluorescent assay (IFA) is the most common serologic test for the detection of Bartonella henselae exposure. It is a highly subjective test, and therefore prone to erroneous interpretation by those who perform the tests. Discrepant sensitivities observed in different laboratories often led to variations in the serologic result interpretation (Amerein et al., 1996; Bergmans et al., 1997; Fournier et al., 2002).

The development of a sensitive and specific assay for the detection of Bartonella henselae has been greatly hampered by the lack of information relating to the characterization of antigens of Bartonella henselae. U.S. Pat. No. 5,736,347 describes the identification of a 17-kDa protein (Anderson et al., 1995; Sweger et al., 2000) which represents one of the few characterized antigens in Bartonella henselae believed to induce antibody responses in humans. However, the '347 patent fails to provide sensitivity and specificity of the full-length 17-kDa protein. Only PCR-dot-blot hybridization and IFA detection assays were performed, hence lacking the necessary affirmation that 17-kDa protein could be a good detection antigen in an ELISA assay, particularly for IgM. Thus, whether the 17-kDa protein serves as antigen to detect an IgM response is far from clear, much less the domain(s) on the 17-kDa protein that is/are responsible for the immunogenic response.

Accordingly, there is a continuing need for an improved assay and a method for the detection of Bartonella henselae. The present invention cures the deficiency of the prior art and provides an unexpected finding that a single domain on the C-terminus of the 17-kDa protein, spanning ~10 amino acids in length, is necessary for the binding of antibodies present in IFA-sero positive sera obtained from patients infected with Bartonella henselae.

SUMMARY OF THE INVENTION

The present invention provides polypeptide fragments of Bartonella henselae that is useful in the detection of Bartonella henselae. The present invention provides recombinant and synthetic polypeptides and methods of using the same in the detection of antibodies specific for Bartonella henselae. The polypeptides, methods and kits are useful in the detection of recent and/or ongoing infections with Bartonella henselae, which can be useful in the diagnosis of CSD.

In one aspect, the present invention provides a synthetic polypeptide having an amino acid sequence as set forth in SEQ ID NO: 22, whereby said synthetic polypeptide, when assayed in an ELISA assay, reacts to IFA sero-positive sera and does not react to IFA sero-negative sera from a patient infected with Bartonella henselae. The polypeptide of SEQ ID NO: 22 contains a segment of 10 amino acids (i.e., EKLE-KSDVRL) which is believed to be necessary (but not sufficient) for the polypeptide of SEQ ID NO: 22 to react to IFA sero-positive sera but not react to WA sero-negative sera from Bartonella henselae-infected patients.

In another aspect, the present invention provides synthetic polypeptides, wherein the synthetic polypeptides contain amino acid substitutions, deletions or additions. The substitution may be a conservative amino acid substitution. The substitution, deletion or addition may involve a single amino acid or multiple amino acids. Preferred embodiment includes SEQ ID NO: 22 having amino acid substitutions, deletions or additions. More preferably, the present invention provides amino acid modification of synthetic polypeptides (i.e., SEQ ID NOs: 24, 25, 26, 27, 28, 29, 30, 31 and 32).

In another aspect, the present invention provides a synthetic polypeptide having an amino acid sequence selected from the group consisting of SEQ ID NO: 24, SEQ ID NO: 25 and SEQ ID NO: 26.

In another aspect, the present invention provides a synthetic polypeptide having an amino acid sequence as set forth in SEQ ID NO: 27.

In another aspect, the present invention provides a synthetic polypeptide having an amino acid sequence as set froth in SEQ ID NO: 32.

In another aspect, the present invention provides a synthetic polypeptide having an amino acid sequence selected from the group consisting of SEQ ID NO: 30 and SEQ ID NO: 31.

In yet another aspect, the present invention provides a recombinant polypeptide containing an amino acid sequence as set forth in SEQ ID NO: 10, whereby said recombinant polypeptide, when assayed in an ELISA assay, reacts to IFA sero-positive sera and does not react to IFA sero-negative sera from a patient infected with *Bartonella henselae.*

In another aspect, the present invention provides recombinant polypeptides, wherein the recombinant polypeptides contain amino acid substitutions, deletions or additions. The substitution may be a conservative amino acid substitution. The substitution, deletion or addition may involve a single amino acid or multiple amino acids. Preferred embodiment includes SEQ ID NO: 10 further comprising amino acid substitutions, deletions or additions. More preferably, the present invention provides amino acid modification of recombinant polypeptides (i.e., SEQ ID NOs: 42, 43, 44 and 45).

In another aspect, the present invention provides a recombinant polypeptide having an amino acid sequence selected from the group consisting of SEQ ID NO: 42 and SEQ ID NO: 43.

In another aspect, the present invention provides a recombinant polypeptide having an amino acid sequence as set forth in SEQ ID NO: 44.

In another aspect, the present invention provides a recombinant polypeptide having an amino acid sequence as set forth in SEQ ID NO: 45.

In yet another aspect, the present invention provides a vector comprising an isolated polynucleotide having a nucleotide sequence as set forth in SEQ ID NO: 9. The vector further comprises a promoter of DNA transcription operably linked to said isolated polynucleotide.

In another aspect, the vector is selected from the group consisting of pET, pENTR, and pC®8/GW/TOPO® and the promoter is selected from the group consisting of lac promoter, trp promoter and tac promoter.

In another aspect, the present invention provides a host cell comprising the vector containing an isolated polynucleotide having a nucleotide sequence as set forth in SEQ ID NO: 9. Preferably, the host cell is *E. coli*. Exemplary *E. coli* includes NovaBlue, BL21 (DE3), or BL21 pLsS (DE3).

In yet another aspect, the present invention provides a method of preparing a recombinant polypeptide having an amino acid sequence as set forth in SEQ ID No: 10, SEQ ID No: 42, SEQ ID No: 43, SEQ ID No: 44, or SEQ ID No: 45, comprising the steps of:
 (a) introducing an isolated polynucleotide into a host cell, said isolated polynucleotide having a nucleotide sequence as set forth in SEQ ID NO: 9; and
 (b) growing said host cell in a culture under suitable conditions to permit production of said recombinant polypeptide; and
 (c) isolating said recombinant polypeptide.

In another aspect, the present invention provides a method for the detection of antibodies specific for *Bartonella henselae* in a biological sample from a mammal. An exemplary method for the detection of antibodies specific for *Bartonella henselae* in a biological sample from a mammal comprises the steps of binding a recombinant polypeptide according to the disclosure to a solid support; contacting the bound recombinant polypeptides to said sample to form antibody-antigen complexes if said antibodies are present in said sample; washing away unbound immunoglobulin; and detecting the presence of any formed antigen-antibody complexes, such as by contacting such complexes with a secondary antibody capable of initiating a visualization reaction, such as a color change of a substrate.

In another aspect, the present invention provides a method for detection of *Bartonella henselae* in a biological sample from a mammal, comprising the steps of:
 (a) immobilizing a synthetic polypeptide to a solid support, wherein said synthetic polypeptide has an amino acid sequence selected from the group consisting of SEQ ID NO: 24, SEQ ID NO: 25, SEQ ID NO: 26, SEQ ID NO: 27, SEQ ID NO: 30, SEQ ID NO: 31, and SEQ ID NO. 32;
 (b) adding a biological sample onto said support to permit antibodies present in said biological sample to bind to said immobilized synthetic polypeptide;
 (c) washing to remove any unbound antibodies; and
 (d) detecting said bound antibodies,
 wherein the presence of bound antibodies is indicative of infection of *Bartonella henselae* of said mammal. Preferably, the mammal is a human.

In yet another aspect, the present invention provides a method for detection of *Bartonella henselae* in a biological sample from a mammal, comprising the steps of:
 (a) immobilizing a recombinant polypeptide to a solid support, wherein said recombinant polypeptide has an amino acid sequence as set forth in SEQ ID NO: 10;
 (b) adding a biological sample onto said support to permit antibodies present in said biological sample to bind to said immobilized synthetic polypeptide;
 (c) washing to remove any unbound antibodies; and
 (d) detecting said bound antibodies,
 wherein the presence of bound antibodies is indicative of infection of *Bartonella henselae* of said mammal. Preferably, the mammal is a human.

In another aspect, the present invention provides a kit. A kit according to an exemplary embodiment comprises a peptide according to the disclosure and instructions for using the peptide in a method according to the disclosure.

In another aspect, the present invention provides a kit useful in the detection of *Bartonella henselae*, said kit comprises:
 (a) a polypeptide having an amino acid sequence as set forth in SEQ ID NO: 22 or SEQ ID NO: 10; and
 (b) an instruction for using the polypeptide in an ELISA assay.

BRIEF DESCRIPTION OF THE DRAWINGS

FIG. 1 depicts the nucleotide and amino acid sequences for the 17-kDa protein in *Bartonella henselae.*

FIG. 4 depicts the nucleotide and amino acid sequences for the recombinant Fragment 1 of the 17-kDa protein in *Bartonella henselae.*

FIG. 7 depicts the nucleotide and amino acid sequences for the recombinant Fragment 2 of the 17-kDa protein in *Bartonella henselae*.

FIG. 8 depicts the nucleotide and amino acid sequences for the recombinant Fragment 4 of the 17-kDa protein in *Bartonella henselae*.

FIG. 9 depicts the nucleotide and amino acid sequences for the recombinant Fragment 3 of the 17-kDa protein in *Bartonella henselae* of present invention.

FIG. 17 is a graph of optical readout data for ELISA assay comparing peptide 3C (A) and peptide 3C-CS1 (B) as coating antigen with IFA positive and IFA negative sera.

FIG. 22 depicts the comparison of amino acid sequences for 17-kDa Fragment 3 between NCBI and the present invention.

FIG. 23 depicts the amino acid sequences for 17-kDa Fragment 3 and its mutations.

FIG. 33 depicts the dot plot illustrating the reactivity of each patient's sera towards 17-kDa polypeptides, 17-kDa Fragment 3, and insertion mutation (immobilized) in an ELISA assay ((A) depicts insertion mutation +V(17-18); and (B) depicts ROC for three polypeptides).

DETAILED DESCRIPTION OF THE INVENTION

Figure 2:
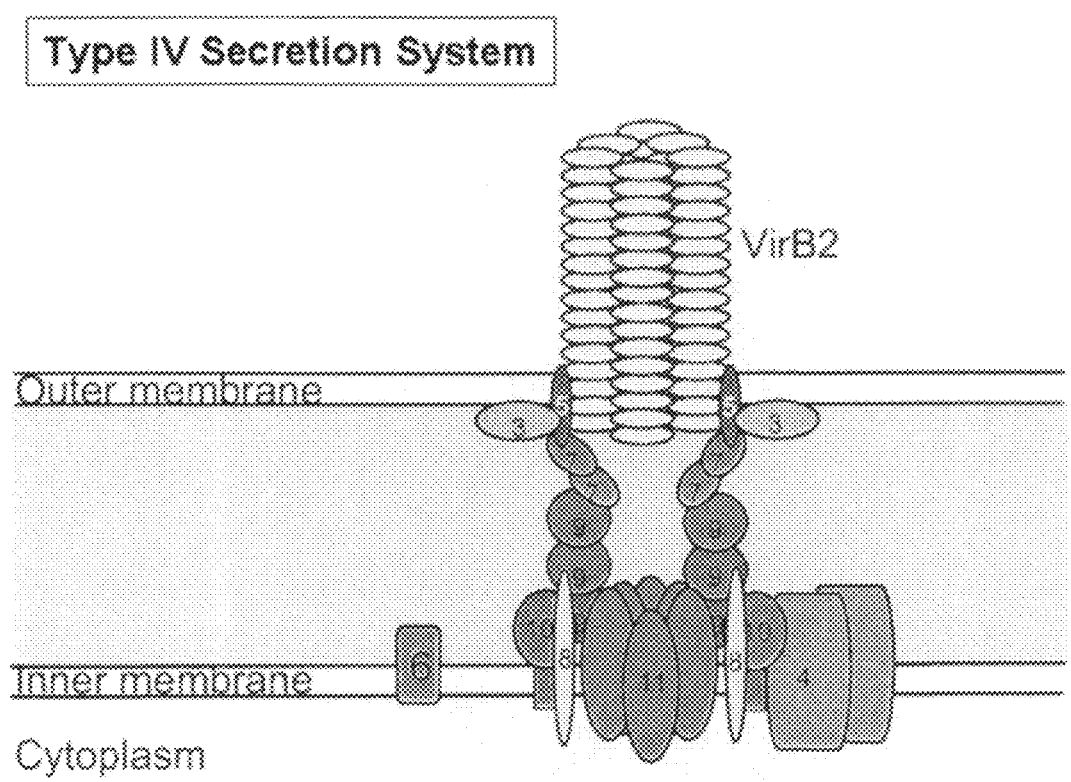
FIG. 2 depicts a schematic diagram of the assembly of the Type IV secretion system in *Bartonella* bacteria (adopted from Shamaei-Tousi et al., *J. Bact.* 186(14): 4796-4801, 2004). According to this model, majority of the virB2 protein is present outside the outer membrane, and the 17-kDa (i.e., virB5) protein is embedded inside the periplasmic membrane.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments of the modifications thereof are contemplated as falling within the scope of the present invention and equivalents thereto. All publications, patent applications, patents, and other references mentioned herein are incorporated by reference in their entirety.

Definitions

Various terms used throughout this specification shall have the definitions set out herein.

As used herein, the term "17-kDa" refers to a polypeptide having an amino acid sequence as set forth in SEQ ID NO: 2 (Accession No. YP_034054). The polypeptide represents the virB5 protein (one of the 12 proteins in Type IV Secretory Protein System) in *Bartonella henselae* strain Houston-1. The 17-kDa polypeptide is shown by the present inventors to bind to antibodies that are present in *Bartonella* patients' sera in an ELISA assay.

As used herein, 17-kDa gene in *Bartonella henselae* strain Houston-1 has a nucleotide sequence as set forth in SEQ ID NO: 1 (Accession No. U23447).

As used herein, the term "ELISA" refers to "Enzyme-Linked ImmunoSorbent Assay" and is a biochemical technique used in detecting the presence of antibody or antigen in a sample.

As used herein, the term "IFA" refers to immunofluorescence assay. "IFA sero-positive sera from a patient" refers to sera (obtained from a patient) that exhibit positive immunofluorescence staining towards cells that have been infected with *Bartonella henselae*. "IFA sero-negative sera from a patient" refers to sera (obtained from a patient) that exhibit negligible immunofluorescence staining towards cells that have been infected with *Bartonella henselae*.

As used herein, the terms "polypeptide," "peptide," or "protein" are used interchangeably.

As used herein, the term "recombinant polypeptide" refers to a polypeptide that is recombinantly expressed by a host cell via the use of a vector that has been modified by the introduction of a heterologous nucleic acid. As used herein, the "synthetic polypeptide" refers to a polypeptide that is synthesized chemically (not a naturally occurring polypeptide). For purposes of the present invention, these polypeptides are intended to encompass polypeptide variations so long as they still possess the ability to bind to antibodies present in Bartonella infected patients in an ELISA assay. One of an ordinary skill in the art would appreciate that the amino acid sequence variations of these polypeptides may include (i) conservative substitutions, (ii) substitution, (iii) addition, and (iv) deletion of amino acids. It would be further appreciated that a polypeptide variant having a sufficiently high % amino acid sequence identity (e.g., >90%) is intended to be encompassed by the present invention, provided that the polypeptide maintains its antibody binding ability.

As used herein, the term "% amino acid sequence identity" is defined as the percentage of amino acid residues that are identical to the amino acid residues in the 17-kDa polypeptide. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "primer" refers to a nucleotide sequence which can be extended by template-directed polymerization. For the purpose of this application, the term "nucleotide sequence" is intended to include DNA or modification thereof.

As used herein, the term "biological sample" may include but are not limited to blood (e.g., whole blood, blood serum, etc), cerebrospinal fluid, synovial fluid, and the like from a mammal such as a human or domestic animal. Extraction of nucleic acids from biological samples is known to those of skill in the art.

As used herein, the term "ROC" refers to Receiver Operating Characteristics Analysis. ROC analysis is a standard statistical tool for evaluation of clinical tests. ROC accesses the performance of the system in terms of "Sensitivity" and "1-Specificity" for each observed value of the discriminator variable assumed as decision threshold (i.e., cutoff value to differentiate between two groups of response). For ELISA, the cutoff value can be shifted over a range of observed values (i.e., $OD_{450}$ nm reading), and Sensitivity and 1-Specificity can be established for each of these values. The optimal pair of Sensitivity and Specificity is the point with the greatest distance in a Northwest direction.

The present invention provides recombinant and synthetic polypeptides that, when assayed in an ELISA assay, react to IFA sero-positive sera and do not react to IFA sero-negative sera from a patient infected with *Bartonella henselae*.

C-Terminus Domain on 17-kDa Protein and Antibody Recognition

In certain embodiments, the protein sequence of the 17-kDa polypeptide is characterized by a hydrophilicity analysis (e.g., Hopp and Woods, 1981, *Proc. Natl. Acad. Sci. U.S.A.* 78:3824). A hydrophilicity profile of 17-kDa is used to identify the hydrophobic and hydrophilic regions, which indicate regions buried in the interior of the folded polypeptide, and regions accessible on the exterior of the polypeptide. Manipulation of the predicted structure can be accomplished using computer software programs available in the art. The degree of antibody binding in an ELISA assay provides information about structural homology, and about the accessibility of regions corresponding to portions of the polypeptide that were used to generate fragment that is specific in antibody recognition.

The present inventors have identified a 10 amino acid region on 17-kDa protein at C-terminal that possesses the required ability to bind to antibodies present in IFA positive sera. In one embodiment, the present invention provides a polypeptide having an amino acid sequence of EKLEKSDVRLA (SEQ ID NO: 33) Accordingly, polypeptides encompassing these 10 amino acid residues represent active polypeptides that can be useful in detection of *Bartonella henselae*, for example, in an ELISA assay. The polypeptide of SEQ ID NO: 33 is by itself insufficient to render the ability to bind antibodies present in IFA positive sera. However, the polypeptide of SEQ ID NO: 22 (which encompasses the 10 amino acids of SEQ ID NO: 33) possesses the ability to bind to antibodies present in IFA positive sera. Thus, the 10 amino acids of SEQ ID NO: 33 are required but not sufficient to render the ability to bind antibodies present in IFA positive sera.

Recombinant Polypeptides

The present invention specifically contemplates expression and preparation of recombinant and synthetic polypeptides, characterized by being capable of binding to antibodies present in IFA positive patient sera. In one embodiment, the present invention thus comprises the isolated nucleic acid having the nucleotide sequence set forth in FIG. 1 (SEQ ID NO: 1), and to degenerate variants, and fragments thereof. The recombinant proteins expressed by the nucleic acids described herein encompasses those proteins set forth in FIG. 1 (SEQ ID NO: 2), as well as variants containing modified amino acids. The recombinant proteins described herein possess the ability to bind to antibodies present in IFA positive sera (and not IFA negative sera), and they contain the 10 amino acid residues (SEQ ID NO: 33).

In one embodiment, the present invention provides a recombinant polypeptide containing an amino acid sequence as set forth in SEQ ID NO. 10.

It is understood that these recombinant polypeptides encompass variants. One type of variants includes modification of amino acids of recombinant polypeptides; such as, for example, substitution, deletion, or addition of amino acids. Another type of variants includes fragments of SEQ ID NO: 10. The variants retain the antibody binding ability towards IFA sero-positive sera and do not react to IFA sero-negative sera from *Bartonella* infected patients. Such recombinant polypeptides are encompassed by the present invention. In one embodiment, conservative amino acid substitutions may be employed, e.g., substituting glutamic acid with aspartic acid; substituting isoleucine with leucine; substituting glycine or valine, or any divergent amino acid, with alanine, substituting arginine or lysine with histidine, and substituting tyrosine and/or phenylalanine with tryptophan. In another embodiment, addition and deletion of single amino acid may be employed. It is also appreciated by one of ordinary skill in the art that a few amino acids can be included or deleted from each or both ends, or from the interior of the polypeptide without altering the peptide's ability to bind antibody, when tested in an ELISA assay.

Recombinant Expression of 17 kDa Polypeptide: Vectors and Hosts

Transcriptional and translational control sequences are DNA regulatory sequences, such as promoters, enhancers, terminators, and the like, that provide for the expression of a coding sequence in a host cell.

A DNA sequence is "operatively linked" or "operably linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted upstream (5') of and in reading frame with the gene.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

In one embodiment, the present invention provides the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and Synthetic DNA sequences. Suitable vectors include pET, pENTR, and pC®8/GW/TOPO® and the like. The promoter contains lac promoter, trp promoter and tac promoter.

In one embodiment, a host cell contains the vector comprising the isolated polynucleotides of the present invention. Exemplary host cell includes *E. coli*. Various *E. coli* strains include, for example, NovaBlue strain, BL21 (DE3) or BL21 pLsS (DE3).

It will be understood that not all vectors, expression control sequences and hosts will function equally well to express the DNA sequences of this invention. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

Synthetic Polypeptides

The present invention provides synthetic polypeptides that have the characteristics of binding to antibodies present in IFA positive patient sera and does not react to IFA negative sera. In one embodiment, the present invention comprises the synthetic polypeptide having at least the amino acid structure set forth in SEQ ID NO: 33. It is understood that synthetic polypeptides may be ~10 to ~30 amino acids in length. Preferably, the synthetic polypeptides may contain 15 to 25 amino acids. Preferably, the synthetic polypeptides may contain 18 amino acid residues.

Preferably, the synthetic polypeptides have the amino acid sequence set forth in SEQ ID NO: 22 and its variants. The synthetic polypeptide variants may contain a substitution, deletion or addition of an amino acid. Preferably, substitution may include a conservative amino acid substitution. Preferably, deletion or addition may include a single amino acid or several amino acids. In one embodiment, the synthetic peptide is SEQ ID NO: 24, SEQ ID NO: 25 and SEQ ID NO: 26, SEQ ID NO: 27, SEQ ID NO: 30, SEQ ID NO: 31, or SEQ ID NO: 32.

The synthetic proteins described herein possess the ability to bind to antibodies present in IFA positive sera (and not WA negative sera), and they contain the 10 amino acid residues (SEQ ID NO: 33).

ELISA Assay

Detection of antibody binding in IFA sero-positive sera may be accomplished by techniques known in the art, e.g., ELISA (enzyme-linked immunosorbent assay), western blots, and the like. In one embodiment, antibody binding is assessed by detecting a label on the primary antibody. In another embodiment, the primary antibody is assessed by detecting binding of a secondary antibody or reagent to the primary antibody. In a further embodiment, the secondary antibody is labeled. Many means are known in the art for detecting binding in an immunoassay and are within the scope of the present invention. For example, to select specific epitopes of recombinant or synthetic polypeptide, one may assay antibody binding in an ELISA assay wherein the polypeptides or its fragments containing such epitope.

Diagnostic Kits Employing Recombinant and Synthetic 17-kDa Polypeptides

The present invention provides a kit for the diagnosis of CSD. In one embodiment, the kit is an ELISA kit containing recombinant or synthetic polypeptides described herein, detection reagents including primary or secondary antibodies, and other necessary reagents including enzyme substrates and color reagents. Additional components that may be present within such kits include an instruction detailing the detection procedure for *Bartonella henselae*, using the recombinant/synthetic polypeptides of the present invention. The diagnostic kit of the present invention further comprises a positive and negative serum control. The diagnostic kit of the present invention can also be used in diagnosing other infectious diseases involving *Bartonella henselae* such as bacillary angiomatosis.

The following Examples are offered by way of illustration and not by way of limitation.

EXPERIMENTAL STUDIES

Example 1

17-kDa Recombinant Fragments 17-kDa gene (FIG. 1) was originally cloned in 1995 (Anderson et al., 1995); however, little is known relating to the function of this protein. The 17-kDa gene locates within a cluster of genes homologous to the virB virulence operon in *Agrobacterium* (Padmalayam et al., 2000). The encoded 17-kDa protein is a component of the Type IV secretion system (TIVSS) in *Bartonella henselae* (FIG. 2), and is a membrane-associated protein complex known to mediate invasion, proinflammatory activation, and anti-apoptotic protection of endothelial cells (Schmid et al., 2004). From its amino acid sequence (FIG. 1), it is inferred that 17-kDa protein lacks a transmembrane domain, does not possess a signal sequence, and is believed to be a soluble protein. Induction of 17-kDa protein was demonstrated in *Bartonella henselae* following its invasion of human endothelial cells (Schmiederer et al., 2001). A study designed to elucidate the interaction between subunits of the TIVSS using a yeast two-hybrid system demonstrated a physical association between virB5 (i.e., 17-kDa) and virB7 (Shamaei-Tousi et al., 2004).

It has previously been shown that the full-length 17-kDa polypeptide can be used in detecting antibodies specific to *Bartonella henselae* in Western blot (U.S. Pat. No. 5,736,347) and ELISA assays (Loa et al., 2005). Because there are very few other immunogenic antigens identified for this human pathogen, further analysis of the epitope(s) of this protein was conducted in an effort to design more effective methods, assays, and kits for the detection of *Bartonella henselae* infections.

Figure 3:
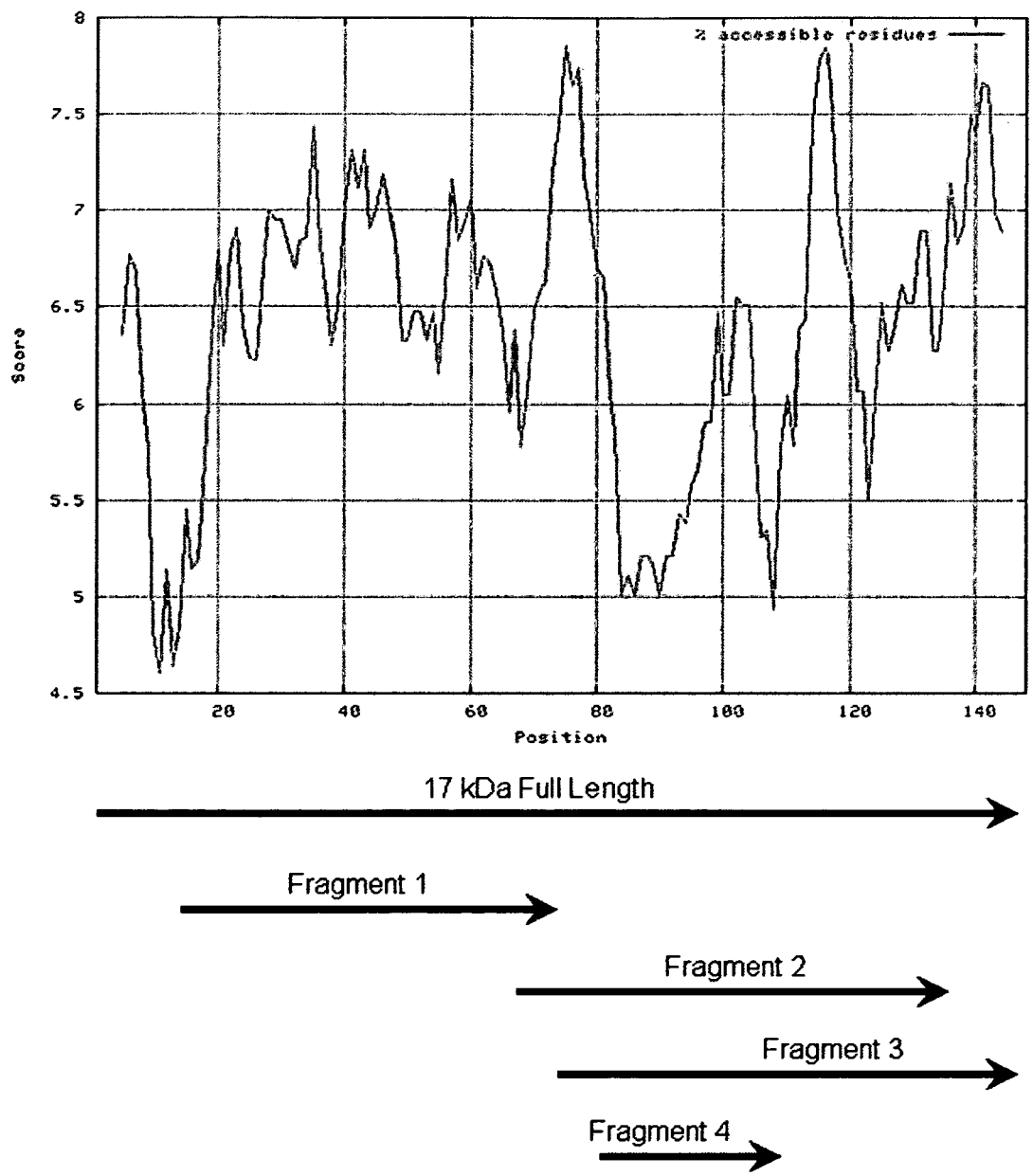
FIG. 3 depicts an accessibility plot showing the full-length 17-kDa protein. The relationship among different recombinant fragments and their accessibility is shown.

Using an in silico approach, a % Accessibility Plot was generated (See, FIG. 3). The plot shows a graphical depiction of two (2) regions of high % accessibility, suggesting that these two regions may be exposed on the 17-kDa protein surface. The first region of high % accessibility encompasses amino acids from about #20 to about #80; and the second region of high % accessibility encompasses amino acids from about #110 to about #140. The region spanning amino acids about #80 to about #110 exhibits low % accessibility.

Based on the % accessibility plot, two (2) recombinant fragments were prepared and they span these two regions of high % accessibility. The two prepared recombinant fragments were then used in an ELISA assay to determine their ability to bind to antibodies present in patients infected with *Bartonella henselae* (i.e., IFA sero-positive). Because the region spanning amino acid #20 to #80 has the highest % accessibility, recombinant Fragment 1 was prepared by PCR cloning (See, FIGS. 3 and 4; details below in Example 2). Fragment 1 spans from amino acid #13 to amino acid #74 (from N-terminal) and contains a total of 62 amino acids. The nucleotide and amino acid sequences of Fragment 1 (SEQ ID NOs: 3 and 4, respectively) are depicted in FIG. 4.

In addition, Fragment 2 was prepared to span the high % accessibility region. Fragment 2 spans from amino acid #63 to amino acid #133. The nucleotide and amino acid sequences of Fragment 2 (SEQ ID NOs: 5 and 6, respectively) are depicted in FIG. 7. Fragment 4 was prepared to cover the low % accessibility region, as a control. Fragment 4 spans from amino acid #81 to amino acid #109. The nucleotide and amino acid sequences of Fragment 4 (SEQ ID NO: 7 and 8, respectively) are depicted in FIG. 8.

In contrast to Fragment 2, Fragment 3 was prepared to cover the second region of high % accessibility. Fragment 3 contains the last 15 amino acid of the C-terminus of 17-kDa protein. When compared to Fragment 2, Fragment 3 lacks the 14 amino acids of the N-terminus of Fragment 2. Fragment 3 spans from amino acid #77 to amino acid #148. The nucleotide and amino acid sequences of Fragment 3 (SEQ ID NOs: 9 and 10) are depicted in FIG. 9.

Example 2

Cloning of 17-kDa Recombinant Fragments

A total of four (4) recombinant fragments were generated (See, FIG. 3). Based on the DNA sequence (SEQ ID NO 1) for the gene that encodes the 17-kDa protein (SEQ ID NO 2), four (4) sets of forward and reverse primers were prepared to amplify the four fragments of the 17-kDa protein from genomic DNA of *Bartonella henselae* (See, Table 1). Each of the primers included LIC extensions on both the 5' and 3' ends to facilitate directional and in-frame cloning into the pET30 Ek/LIC vector (described in details below). Table 1 lists the nucleotide sequences for these four (4) sets of forward and reverse primers.

TABLE 1

Primers for Generation of Polynucleotides Encoding Four (4) Recombinant Fragments of the 17-kDa protein of *Bartonella henselae*

| Fragments | Primers | Nucleotide sequences | SEQ ID NOs |
|---|---|---|---|
| | Forward | GACGACGACAAGATGGCTGCCTATATTTCATC | SEQ ID NO: 11 |
| | Reverse | GAGGAGAAGCCCGGTCTTAATTTTGTTTGCAGT | SEQ ID NO: 12 |
| | Forward | GACGACGACAAGATGACATAAACAATCAACTTG | SEQ ID NO: 13 |

TABLE 1-continued

Primers for Generation of Polynucleotides Encoding
Four (4) Recombinant Fragments of the 17-kDa protein
of *Bartonella henselae*

| 17-kDa Fragments | Primers | Nucleotide sequences | SEQ ID NOs |
|---|---|---|---|
| | Reverse | GAGGAGAAGCCCGGTGAAGATCTTCATGCTTT | SEQ ID NO: 14 |
| 3 | Forward | GACGACGACAAGATGACTAAACCTGAACAATTG | SEQ ID NO: 15 |
| | Reverse | GAGGAGAAGCCCGGTCTAAGTCGGACATCAG | SEQ ID NO: 16 |
| 4 | Forward | GACGACGACAAGATGAACAATTGCAAGCCC | SEQ ID NO: 17 |
| | Reverse | GAGGAGAAGCCCGGTCATAGCAAGAGACTGG | SEQ ID NO: 18 |

Cloning inserts including polynucleotides encoding the four (4) recombinant fragments were prepared using the primer sets listed in Table 1 in Polymerase Chain Reaction (PCR) procedures. Briefly, for Fragment 1, genomic *Bartonella henselae* template DNA was denatured at 94° C. for 2 minutes. A standard PCR procedure was then conducted with the primers listed in Table 1 for Fragment 1 using thirty cycles of denaturing at 94° C. for 30 seconds, annealing at 54° C. for 30 seconds, and extending at 68° C. for 1 minute. After the PCR procedure, samples were incubated at 68° C. for 10 minutes to complete DNA synthesis. The expected amplicon size of 218 base pair was confirmed by agarose gel electrophoresis.

For Fragment 2, touchdown PCR was used to produce a cloning insert. Briefly, genomic *Bartonella henselae* template DNA was denatured at 94° C. for 3 minutes. A standard PCR procedure was then conducted with the primers listed in Table 1 for Fragment 2 using multiple cycles of denaturing at 94° C. for 30 seconds, touchdown annealing temperature for 30 seconds, and extending at 72° C. for 90 seconds. The annealing temperature in the initial cycle was 64° C. and was decreased by 1° C. each cycle and repeated three times at each annealing temperature. This was repeated 29 times; the final touchdown annealing temperature was 54° C. After the PCR procedure, samples were incubated at 72° C. for 5 minutes to complete DNA synthesis. The expected amplicon size of 245 base pair was confirmed by agarose gel electrophoresis.

A cloning insert for Fragment 3 was prepared using the same PCR conditions described above for Fragment 1. The expected amplicon size of 248 base pair was confirmed by agarose gel electrophoresis.

A cloning insert for Fragment 4 was prepared using the same PCR conditions described above for Fragment 2. The expected amplicon size of 119 base pair was confirmed by agarose gel electrophoresis.

Figure 16:
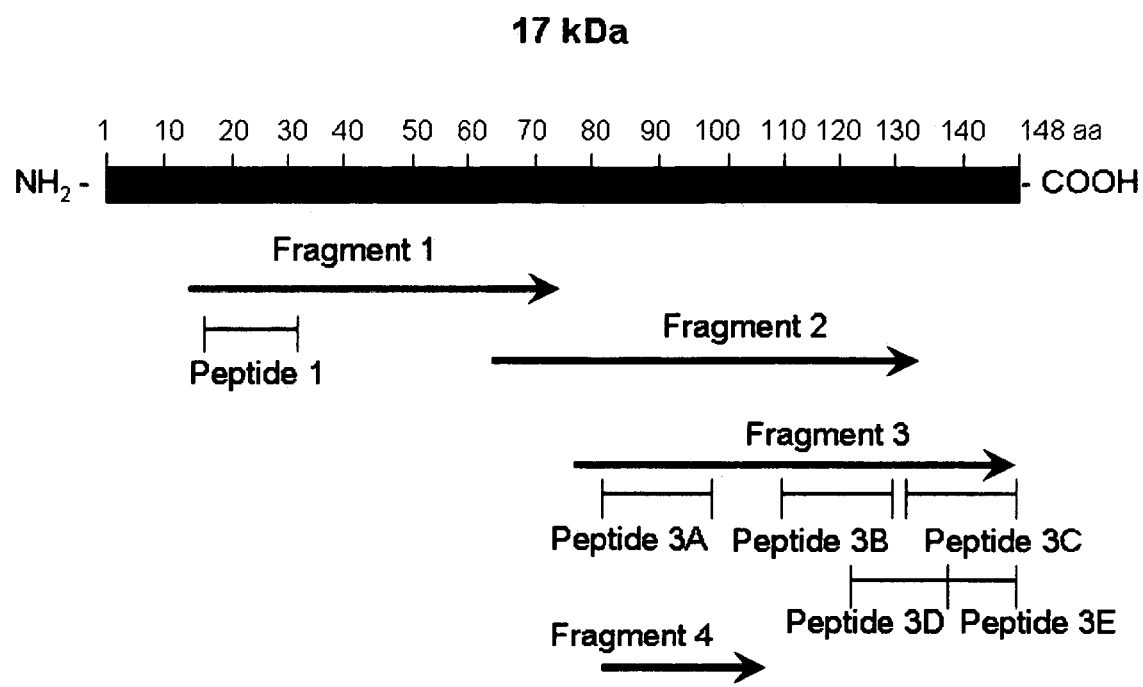
FIG. 16 depicts the relationship between various synthetic polypeptides and recombinant 17-kDa protein Fragments.
Figure 18:
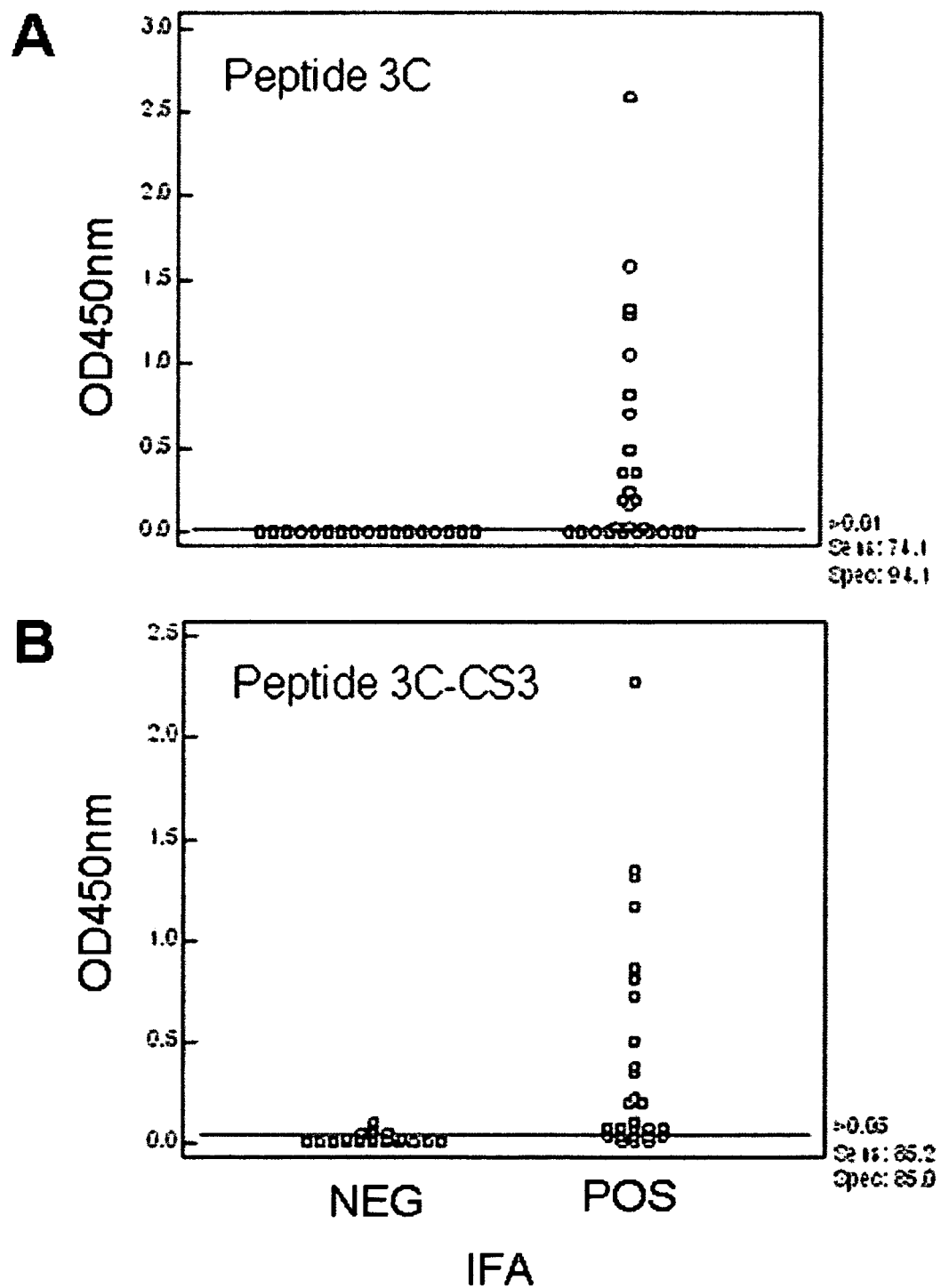
FIG. 18 depicts the dot plot illustrating the reactivity of each patient's sera towards 17-kDa polypeptides (immobilized) in an ELISA assay ((A) depicts peptide 3C; (B) depicts peptide 3C-CS3; (C) depicts peptide 3C-Del; and (D) depicts peptide 3C-RD).
Figure 18:
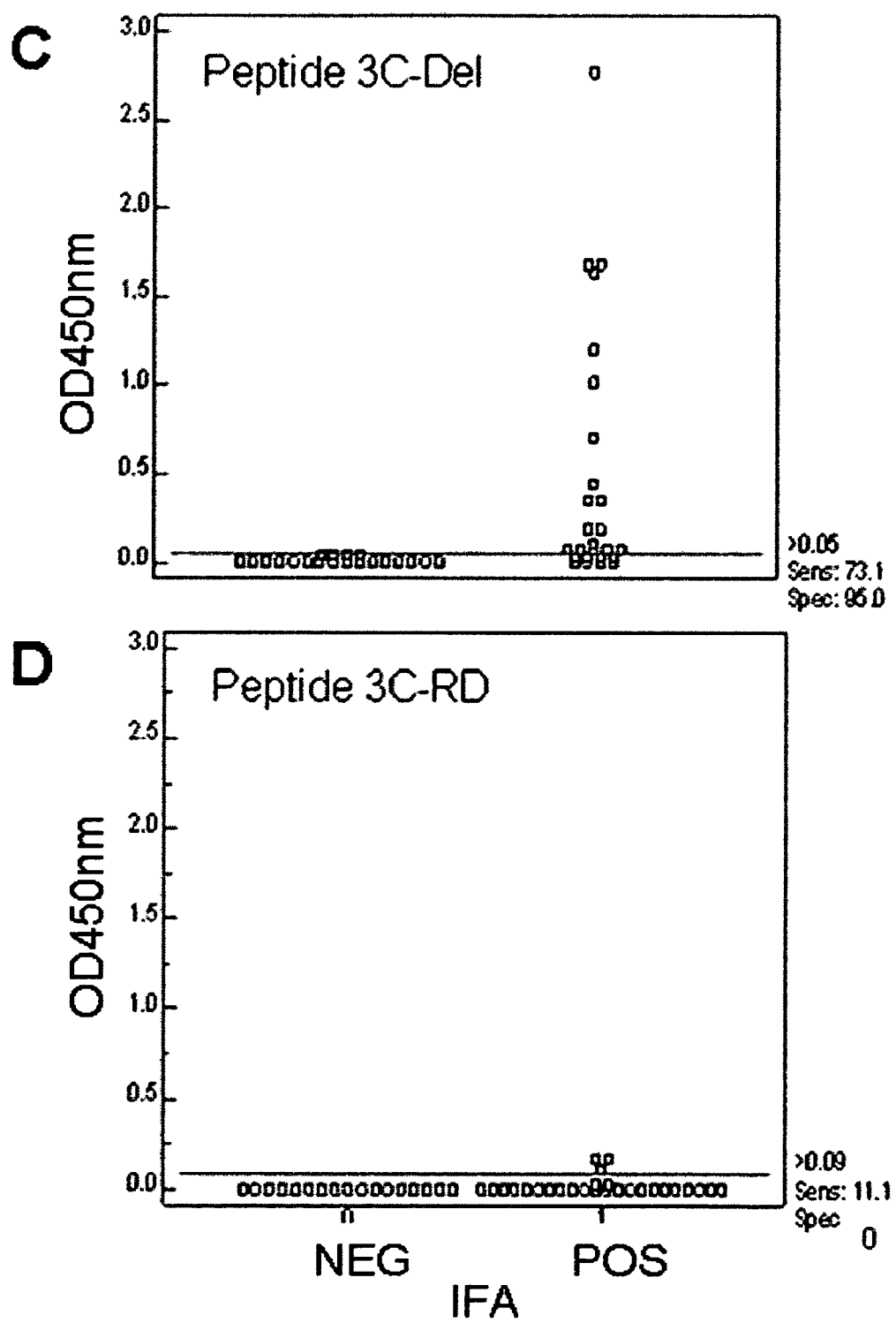
Figure 18:
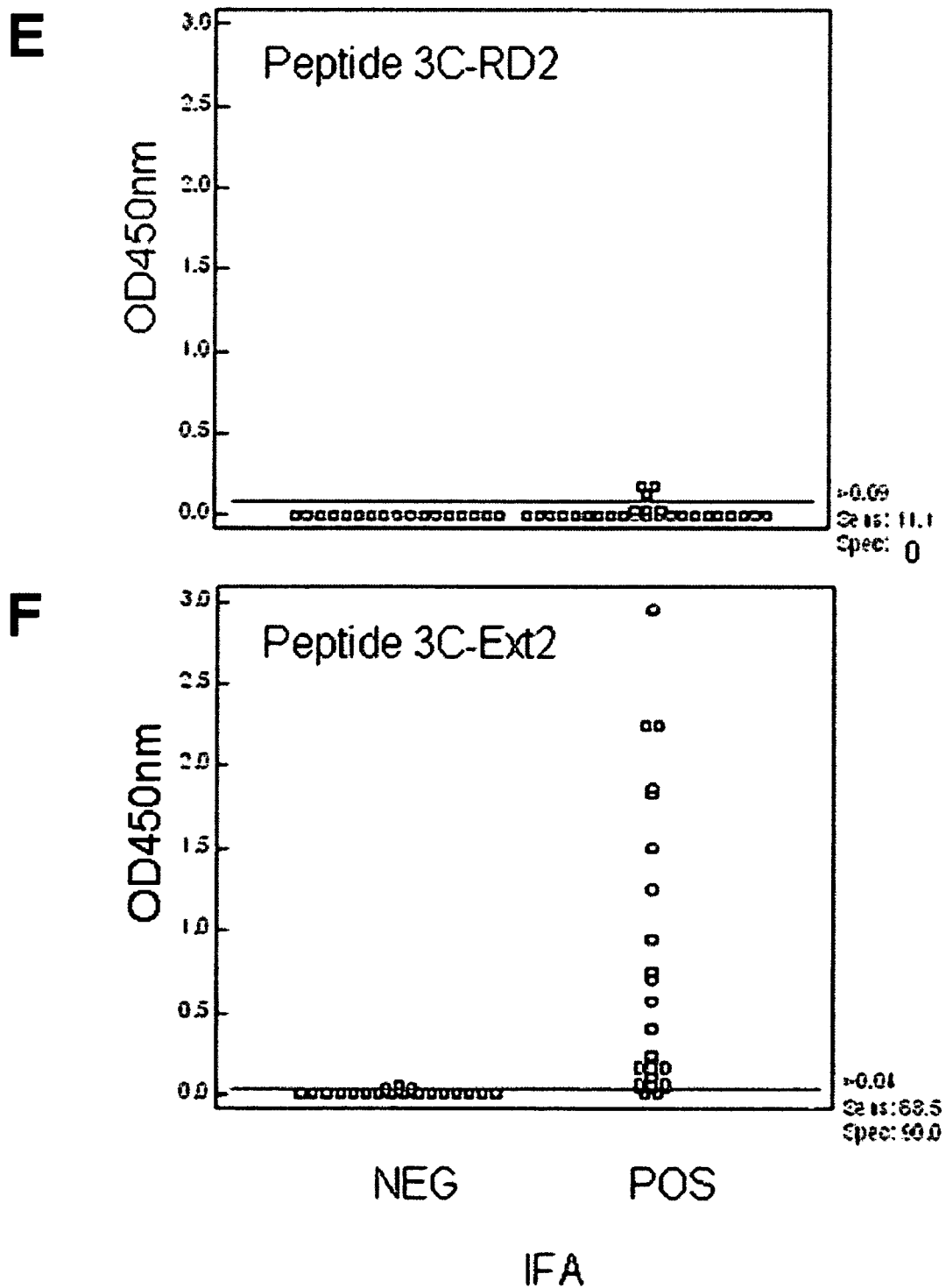

As illustrated in the FIG. 3 and Table 2, the full-length 17-kDa protein in *Bartonella henselae* strain Houston-1 is composed of 148 amino acids. Fragment 1 spans from amino acid #13 to amino acid #74 (from N-terminal) and contains a total of 62 amino acids. Fragment 2 spans from amino acid #63 to amino acid #133 and contains a total of 71 amino acids. Fragment 3 spans from amino acid #77 to amino acid #148 and contains a total of 72 amino acids. Fragment 4 spans from amino acid #81 to amino acid #109 and contains a total of 29 amino acids (See, FIG. 16).

TABLE 2

Amino Acid and Nucleotide Position for Polypeptides

| Protein Name | Protein Position (aa) | DNA Position (bp) |
|---|---|---|
| 17-kDa Full Length | 1-148 | 1-444 |
| 17-kDa Fragment 1 | 13-74 | 37-222 |
| 17-kDa Fragment 2 | 63-133 | 187-399 |
| 17-kDa Fragment 3 | 77-148 | 229-444 |
| 17-kDa Fragment 4 | 81-109 | 241-327 |
| Synthetic Peptide 1 | 15-32 | 43-96 |
| Synthetic Peptide 3A | 81-98 | 241-294 |
| Synthetic Peptide 3B | 111-128 | 331-384 |
| Synthetic Peptide 3C | 131-148 | 391-444 |
| Synthetic Peptide 3D | 123-138 | 367-414 |
| Synthetic Peptide 3E | 139-148 | 415-444 |

Using PCR, four (4) fragment inserts were obtained. Using agarose gel electrophoresis, Fragment 1 was confirmed to be 218 base pairs in length, Fragment 2 was confirmed to be 245 base pairs in length, Fragment 3 was confirmed to be 248 base pairs in length, and Fragment 4 was confirmed to be 119 base pairs in length (See, FIG. 16). These fragments include franking sequences. Excess primers and DNA polymerase were removed using the Wizard PCR Clean-up kit (Promega) in preparation for cloning.

For cloning and expression, the pET30 Ek/LIC vector was selected because it affords protein expression and provides for rapid purification of expressed protein by His.Bind resin chromatography.

Figure 5:
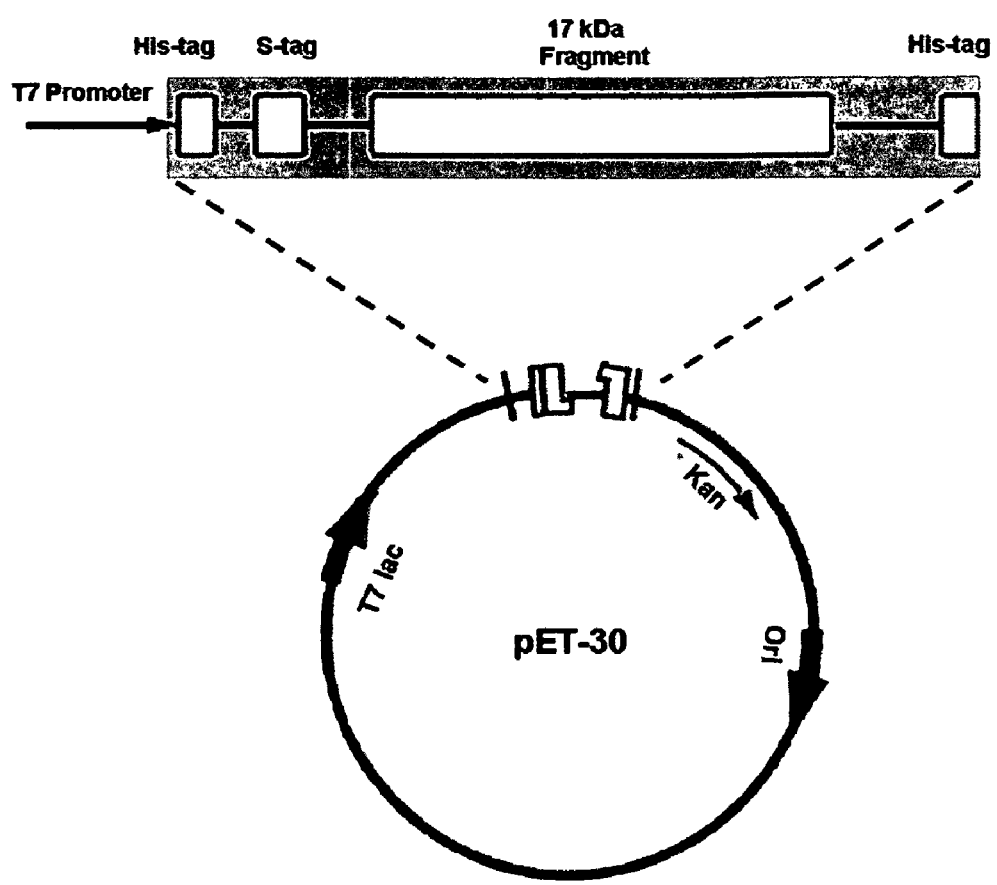
FIG. 5 is a schematic of the vector used for the cloning and expression of the recombinant polypeptides of 17-kDa fragments expressed herein.

FIG. 5 is a schematic of the pET30 expression vector. As a preparatory step, each of the purified PCR products (i.e., 218 bp, 245 bp, 248 bp, and 119 bp) was treated with T4 DNA polymerase to create overhangs complementary to the expression vector. Briefly, a reaction consisting of purified PCR product, T4 DNA polymerase buffer, dATP, DTT, and T4 DNA polymerase (LIC-qualified) was prepared for each PCR product in a final reaction volume of 20 μl. The reaction was started by adding enzyme, followed by incubation at room temperature for 30 minutes. To complete the reaction, the T4 DNA polymerase was inactivated by incubating the reaction mixture at 75° C. for 20 minutes.

To link pET30 vector and Ek/LIC insert, a reaction was set up consisting of pET-30 Ek/LIC vector, T4 DNA polymerase treated Ek/LIC insert DNA. The reaction was initially incubated at room temperature for 5 minutes. 25 mM EDTA was then added, and the reaction was then incubated at room temperature for an additional 5 minutes. Treated PCR products were then incubated with the pET30 Ek/LIC vector to allow annealing.

The ligation products were then transformed into NovaBlue *E. coli*. Briefly, 20 µl aliquots of NovaBlue *E. coli* competent cells were removed from −80° C. Aliquots were thawed on ice for several minutes, followed by the addition of 1 µl annealing product with gentle stirring. The mixture was incubated on ice for 5 minutes before being heated in a 42° C. water bath for 30 seconds. Next, the samples were immediately placed back on ice for 2 minutes. To recover *E. coli* from the heat shock, 80 µl SOC (at room temperature) was added and the mixture was incubated at 37° C. with shaking (250 rpm) for 1 hour. Finally, transformed *E. coli* was plated to LB agar plates containing 30 µg/ml kanamycin and incubated overnight at 37° C.

Plasmid DNA was isolated from transformed *E. coli* using Wizard Plus SV Minipreps DNA Purification system (Promega) following the manufacturer's recommended protocol. The purity of DNA plasmid was identified by photometer reading ($OD_{260}/OD_{280}$ ratio). To check size of plasmid DNA, circular DNA was linearized with Kpn I or digested with EcoR I. Migration position of plasmid DNA was confirmed by comparing to standard molecular weight markers in agarose gel electrophoresis.

Figure 6:
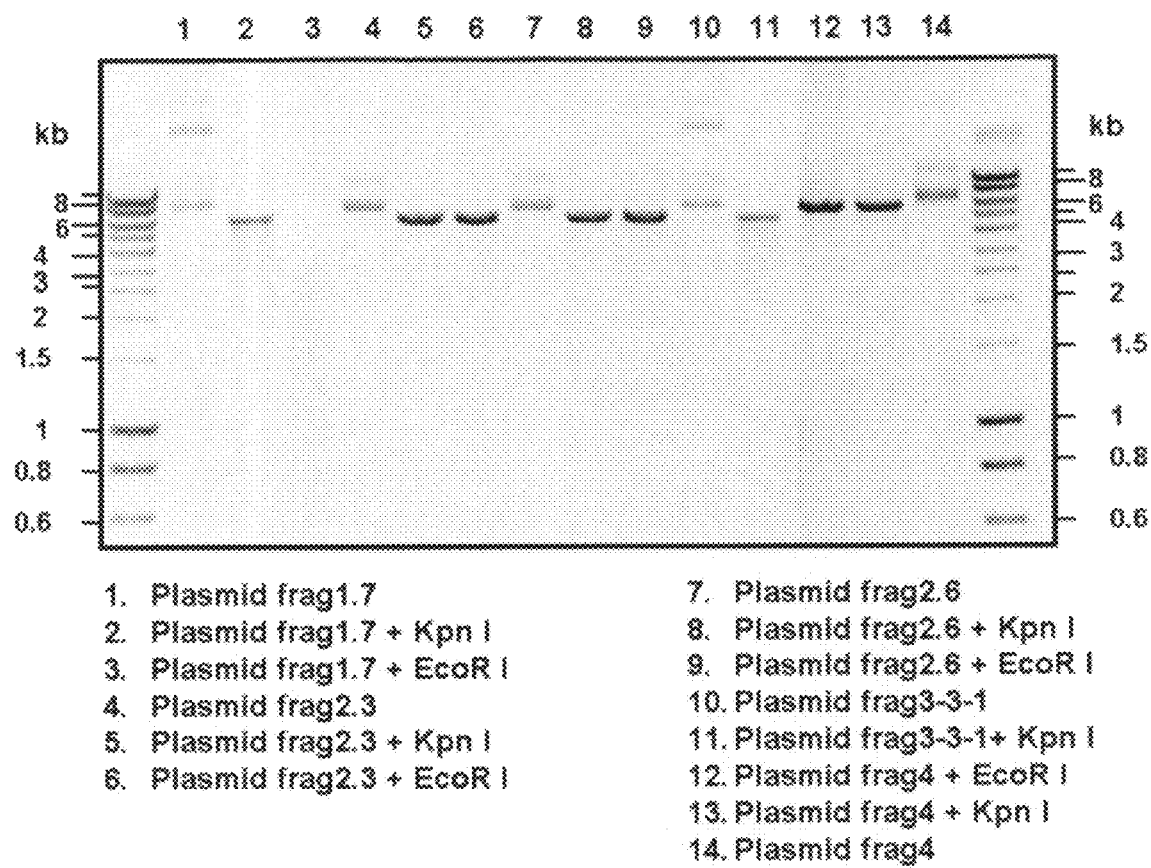
FIG. 6 is a 1% agarose gel analysis of 17-kDa fragment in pET30 EK/LIC vector, showing migration of circular and linearized plasmid DNA samples from transformed *E. coli* cells.

As shown in FIG. 6, the linear DNA of each recombinant plasmid migrated between 5-6 kb according to DNA marker. This 119-248 bp corresponds to the expected clone size because pET30 vector (5,439 bp) plus insert is about 5,558-5,687 bp. Finally, every base pair of each fragment ORF was confirmed correct by DNA sequencing using a 3130 Genetic Analyzer DNA Sequencing instrument and Lasergene sequence alignment analysis.

Cloning vectors were transformed into expression system BL21 (DE3) *E. coli* using the procedure described for NovaBlue *E. coli* system, except that 1 µl of plasmid DNA (100 ng/µl) was incubated with 20 µl BL21 (DE3) *E. coli*.

Example 3

Expression of 17-kDa Recombinant Fragments

The Overnight Express Autoinduction System was used to induce expression of the cloned fragments. The system is designed for high-level protein expression and eliminates the need to monitor cell growth. Complex medium was prepared as 1 ml OnEx Solution 1, 2.5 ml OnEx Solution 2, 0.05 ml OnEx Solution 3, 46.45 ml LB broth, and 50 µl of 30 mg/ml kanamycin. All components for complex medium were added and mixed aseptically. To start the cultures, a glycerol stock of BL21 (DE3) transformed with pET30-17-kDa fragment plasmid was inoculated into 2 ml LB broth containing kanamycin. Starter culture was incubated at 37° C. with shaking at 250 rpm to an $OD_{600}$ of approximately 0.5. 1 ml of the starter culture ($OD_{600}$=0.5) was then added into 50 ml o/n complex medium at 37° C. with shaking at 250 rpm for about 17 hours. *E. coli* cells were harvested by spinning at 10,000×g for 10 minutes at 4° C. The expression of target protein was positively confirmed by SDS PAGE before purification.

a) Failure of Recombinant Expression for Fragments 1, 2 and 4

To our surprise, Fragment 1 failed to express, neither did Fragments 2 and 4. These fragments were designed because they possess high % accessibility and they were expected to possess antibody binding sites. Poor solubility was ruled out as a reason for the lack of recombinant expression. The exact reasons for the failure are presently unknown; we speculated that codon bias or toxicity of the fragments to *E. coli* may adversely affect the recombinant expression. As such, these recombinant fragments may possess unique characteristics that prevent them to be recombinantly expressed.

b) Successful Recombinant Expression for Fragment 3

We unexpectedly discovered that Fragment 3 could be successfully expressed using the Overnight Express Autoinduction System I. Given the close similarity of polynucleotide sequences between Fragment 2 and Fragment 3, it was a total surprised finding that only Fragment 3 would be expressed.

Figure 10:
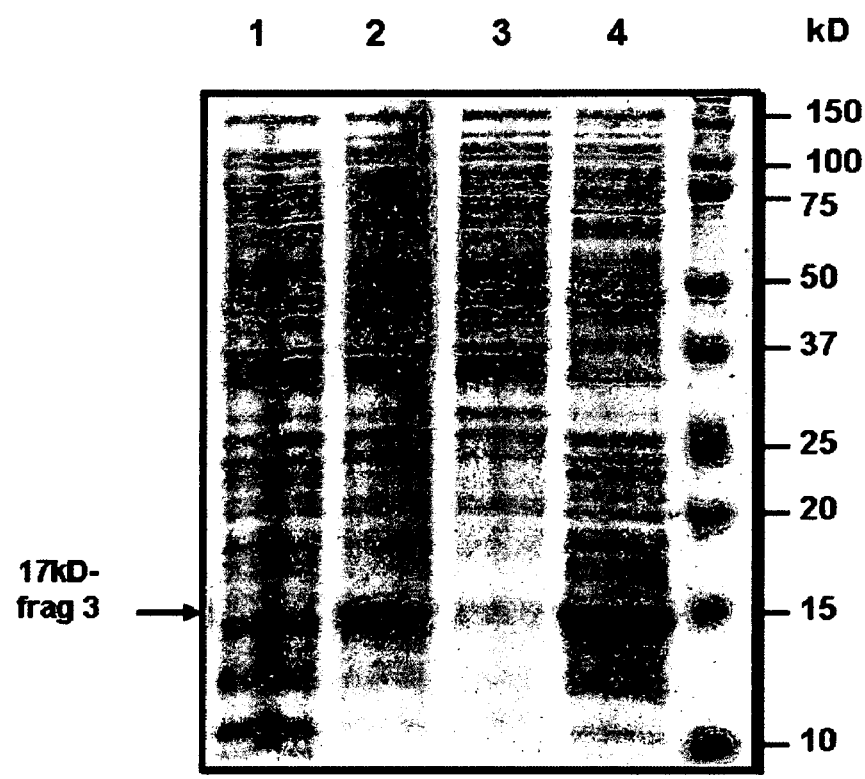
FIG. 10 is Coomassie blue-stained SDS electrophoresis gel showing induced expression of recombinant Fragment 3 in transformed *E. coli* cells.
Figure 11:
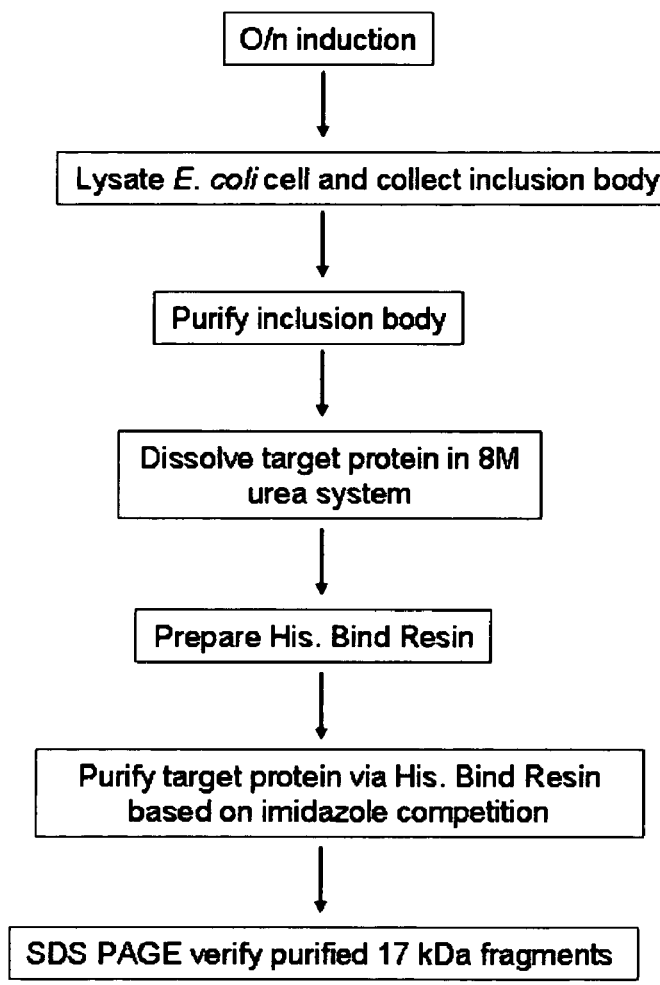
FIG. 11 depicts a purification scheme for the 17-kDa recombinant protein fragments following expression.

The migration mass of recombinant Fragment 3, which contains His-tag, was about 15 kDa in SDS electrophoresis gel (FIG. 10). It was determined that this fragment was present almost 100% as an insoluble formation in cytoplasmic inclusion body (FIG. 10, lanes 3 & 4). This formation of inclusion body may be due to aggregation of over-expressed target protein. To purify induced protein from whole *E. coli* lysate, the inclusion body pellet was denatured and dissolved with 8M urea and the sample was passed over a His.Bind resin column under same denaturing condition (8M urea).

Table 3 presents a qualitative assessment of the induction of expression of recombinant Fragments 1, 2, 3, and 4 in transformed cells. Only Fragment 3 was successfully expressed using the Overnight Express Autoinduction System I (Table 4, FIG. 10, lanes 1-2). IPTG express induction of Fragments 1, 2 and 4 was attempted, but also proved unsuccessful.

TABLE 3

Qualitative Assessment of Induction of Expression of Recombinant 17-kDa Fragments in Transformed Cells

| 17-kDa Recombinant Polypeptides | Overnight Induction | IPTG Induction |
|---|---|---|
| Fragment 1 | — | — |
| Fragment 2 | — | — |
| Fragment 3 | +++ | *NT |
| Fragment 4 | — | — |

*NT = not tested

Example 4

Purification of 17-kDa Recombinant Fragments

Because the recombinant Fragment 3 formed aggregations in inclusion bodies after it was expressed in BL21 (DE3) *E. coli*, we took steps to solubilize the recombinant Fragment 3 protein. Purification of this recombinant protein was conducted under denaturing conditions. Nickel chelating affinity chromatography was used to capture the protein via interaction with the 6×his tag (i.e., histidine tag) on the end terminus. Briefly, recombinant protein was released from the cell using BugBuster MasterMix (Novagen). The cell pellet from spin down was re-suspended in 5 ml BugBuster MasterMix by gentle pipette mixing. Cell lysis was completed by incubating it in BugBuster with rotating mixing for 20 minutes at room temperature. The mixtures were centrifuged at 4° C. for 20 minutes at 11,800 rpm with SS-34 rotor to separate insoluble part from soluble component. Both soluble and insoluble fraction was transferred to a fresh tube for SDS PAGE analysis.

To purify the inclusion body (containing aggregated protein), the insoluble pellet fraction was re-suspended in same volume (5 ml) BugBuster MasterMix. The mixture was gently pipetted to an even suspension before it was incubated at room temperature for 5 minutes. 20 ml BugBuster MasterMix (1:10 diluted in water) was added and the suspension was gently mixed. The insoluble fraction was centrifuged down at 5,000×g for 15 minutes at 4° C. The pellet was resuspended in 15 ml diluted BugBuster MasterMix, pipette mixing, and centrifuged at 5,000×g for 15 minute at 4° C. This step was repeated and the pellet was then resuspended in 10 ml bind buffer without urea. The purified inclusion body was spun down at 16,000×g for 15 minutes at 4° C. 2.5 ml bind buffer with 8 M urea was added to the pellet and incubated with rotation at 4° C. for 1 to 2 hours to completely dissolve protein. Insoluble material was removed by spinning at 16,000×g for 30 minutes at 4° C. The supernatant was then passed through a His.Bind resin column. An aliquot of the purified inclusion body fraction was analyzed on an SDS PAGE gel.

Small scale purification of target protein was carried out under denaturing condition (8 M urea). The inclusion body pellet from 50 ml overnight induction culture was re-suspended in 2.5 ml of bind buffer (8 M urea). To this mixture was added 250 µl of charge prepared His.Bind slurry (Novagen). The suspension was mixed gently on a rotating shaker for 0.5 hour at room temperature. This lysate-resin mixture was placed into a column which was then placed into a 15-ml conical tube. The flow-through was collected and saved for gel analysis. Afterwards, the column was washed with 2×1.25 ml bind buffer (8 M urea). Then the column was eluted/washed with 2×1.25 ml of wash buffer (8 M urea). 5×0.125 ml of elution buffer I (8 M urea) containing 250 mM imidazole was passed through the column to extract recombinant protein from the His.Bind resin. Two elution steps were performed in order with 0.125 ml elution buffer II (pH 5.9, 8 M urea) and 0.125 ml elution buffer III (pH 4.5, 8 M urea) to confirm the complete recovery of target protein from His. Bind resin.

Figure 12:
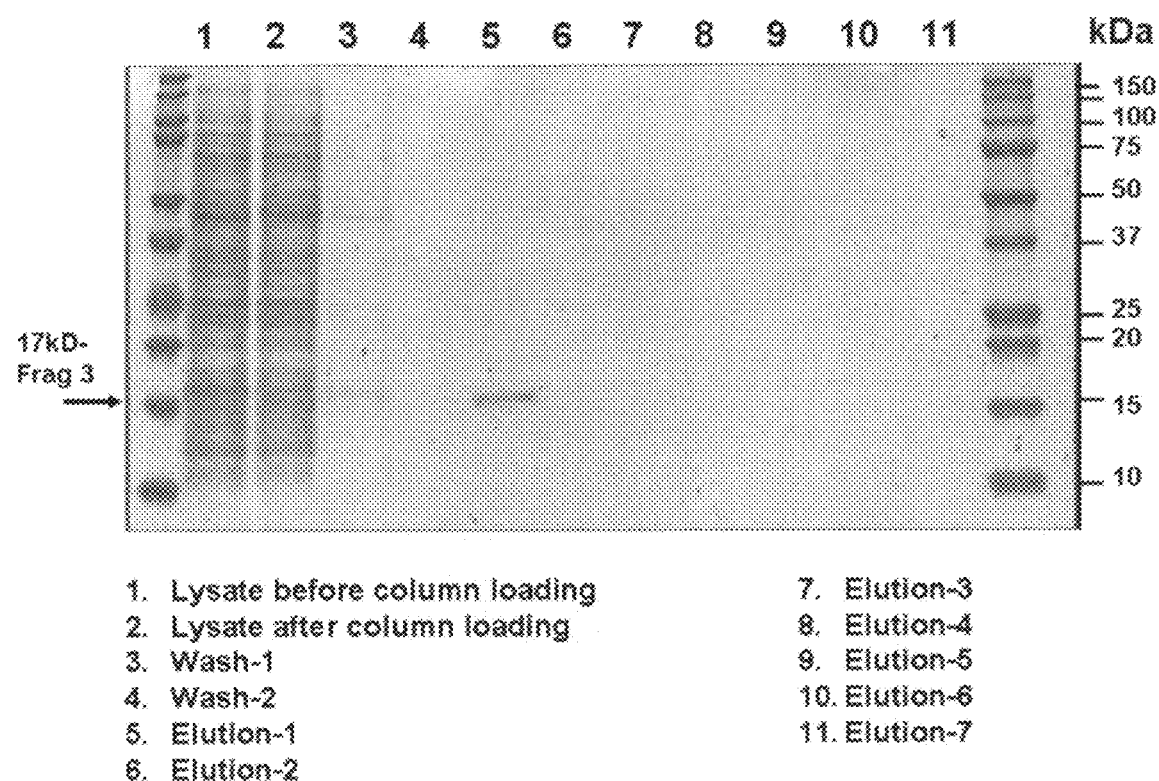
FIG. 12 is a Coomassie blue-stained SDS PAGE gel of elution samples from each step of a small scale purification of recombinant Fragment 3 protein.

FIG. 12 presents a Coomassie blue-stained SDS gel SDS PAGE analysis conducted on each step of small scale purification of recombinant Fragment 3 protein.

A large scale purification of Fragment 3 was also successfully carried out from inclusion body under denaturing conditions (8 M urea). His.Bind resin was prepared by loading 1 ml His.Bind resin slurry into a column. The resin was washed with 3 ml distilled pure water. 5 ml of charge buffer was passed through, and the resin was equilibrated with 3 ml of bind buffer.

Figure 13:
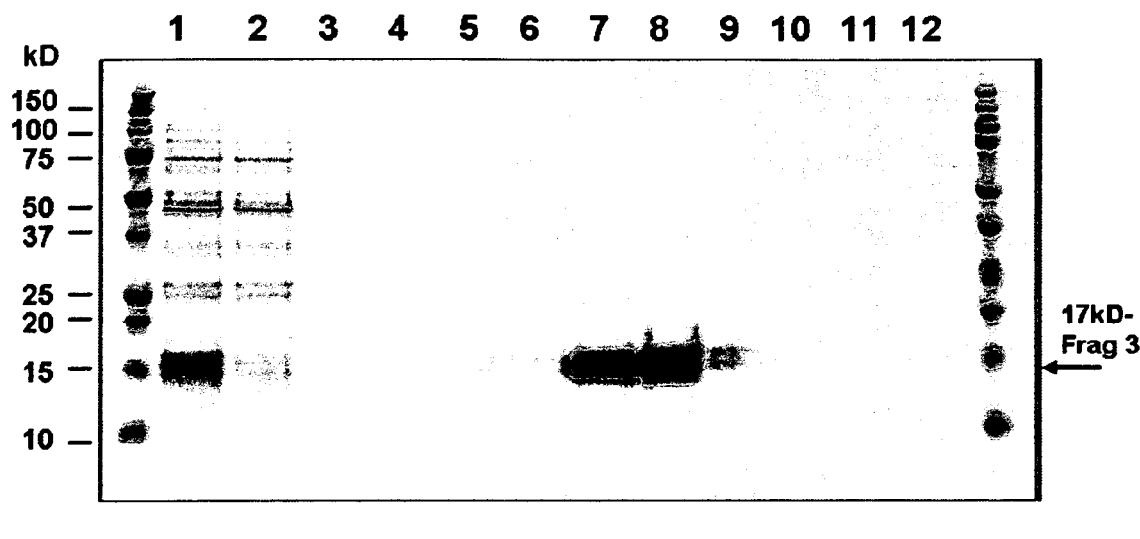
FIG. 13 is a Coomassie blue-stained SDS PAGE gel of elution samples from each step of a large scale purification of recombinant Fragment 3 protein.

The inclusion body pellet from 500 ml overnight (o/n) induction culture was re-suspended in 15 ml bind buffer (8 M urea). 1 ml charge prepared His. Bind slurry was added to this mixture. The suspension was mixed gently on a rotating shaker for 30 minutes in room temperature. Lysate-resin mixture was loaded onto same column placed over a 15-ml conical tube and the mixture was allowed to drain through the column. The column was washed with 2×5 ml bind buffer (8 M urea). 2×4 ml wash buffer (8 M urea) was passed through the same column. The recombinant protein was eluted with 6×0.5 ml elution buffer I (8 M urea). FIG. 13 is a Coomassie blue-stained SDS gel SDS PAGE analysis conducted on each step of large scale purification of recombinant Fragment 3.

In both small and large scale purifications, SDS-PAGE analysis show a major protein band with a molecular mass of approximately 15 kDa, which is similar to the expected fusion protein comprising the recombinant Fragment 3 coupled to a histidine tag.

Example 5

IgG ELISA Analysis of 17-kDa Recombinant Fragments (I) Recombinant Fragments 1 (Amino Acid #20 to #80), 2 (Amino Acids #63 to #133) and 4 (Amino Acids #81 to #109) Fail Protein Expression Recombinant Fragment 1 spans one high % accessibility area, and recombinant Fragment 2 spans the other high % accessibility area on the 17-kDa protein (See, FIG. 3). Unfortunately, expression of these recombinant fragments was unsuccessful. No detectable amount of recombinant fragments 1 and 2 was observed in either soluble or insoluble (inclusion bodies) fractions. Multiple efforts were undertake to optimize the expression of these recombinant fragments. This included: (i) varying the IPTG concentration; (ii) altering the duration of induction (iii) using a different expression system (i.e., Overnight Autoinduction Expression System), which uses a different inducer (i.e., glucose). All these attempts proved to be unsuccessful.

Colony PCR was performed on plasmids isolated from host cells transformed with each of the recombinant fragments to confirm that the host cells were transformed with recombinant vectors. Because the pET30 vector harbors the kanamycin antibiotic resistance gene, the growth of host cells in the presence of antibiotic (added to the LB medium) confirmed that these cells were successfully transformed with recombinant vector. Furthermore, an additional confirmation for the successful transformation of recombinant Fragments 1 and 2 was the sequencing of both fragments. This was performed in both forward and reverse directions, and the open reading frame (ORF) within each insert was confirmed to be correct and in proper frame of the his-tag sequence. Accordingly, the lack of expression could not be attributed to (1) failure to clone insert DNA into vector (2) unsuccessful transformation of host cells, (3) presence of an in-frame Stop codon leading to production of a truncated protein (either with or without histidine tag). It was speculated that unpredictable factors, including intrinsic property of the 17-kDa protein, may have attributed to the failure of the recombinant fragments to be expressed.

Despite best efforts, recombinant Fragments 1 and 2 could not be expressed. These two recombinant fragments together span a majority (i.e., ~90%) of the entire length of 17-kDa protein. We next made another attempt to determine if recombinant Fragment 4 (amino acids #81 to #109) (predominantly inaccessible amino acids; See, FIG. 3) may possess antibody binding activity. Similar to recombinant Fragments 1 and 2, recombinant Fragment 4 fails to be expressed.

(II) Recombinant Fragment 3 (Amino Acids #77 to #148)

The studies described above made clear that recombinant Fragments 1, 2 and 4 fail to be expressed. Given that Fragment 1 and Fragment 2 together span a majority (133/148; ~90%) of the entire length of 17-kDa protein, it was concluded that the recombinant fragment approach may have failed.

In particular, it was not expected that the last 15 amino acids at the C-terminal could have rescued Fragment 2's ability to be expressed, much less that these 15 amino acids account for the antibody binding activity (i.e., active region on the 17-kDa).

Because the 15 amino acid length was too short to be cloned, recombinant Fragment 3 was prepared. This recombinant fragment includes the 15 amino acids at the C-terminus. We then tested this fragment's ability to bind antibodies in an ELISA assay.

In the ELISA assay, purified Fragment 3 protein was diluted in coating buffer to a final concentration of 250 ng/ml. Antigen was adhered to 96-well plate by applying 100 μl this solution per well and incubated at 4° C. for 18 hours. Uncoated antigen was removed by washing the plate three times with PBST wash buffer. After washing, post-coating was done with 300 μl blocking reagent General Blocker BB1 in each well for 1 hour at 22° C. Primary polyclonal antibody from 100 μl serum in 1:100 sample dilution buffer each well was allowed to react with coated antigen for 1 hour at 22° C. After five wash steps with PBST wash buffer, each well was incubated with 1000 peroxidase conjugated goat anti-human IgG (KPL, 1:20,000 from 1 mg/ml stock in sample dilute buffer) for 30 minutes at 22° C. The excess amount of secondary antibody was also removed by five wash steps with PBST wash buffer. The reaction were visualized by adding 100 μl substrate 3,3'5,5'-Tetramethylbenzidine solution and incubated at 22° C. for 15 minutes. The reaction was terminated by adding 100 μl 0.5 M $H_2SO_4$ per well before taking $OD_{450nm}$ measurement. Receiver operating characteristic curve (ROC) analysis was calculated with associated 95% confidence interval using a binomial distribution with the MedCalc program.

It was a surprised finding to find that recombinant Fragment 3 (differs slightly from Fragment 2) (See, FIG. 16) could be expressed. Furthermore, it was an unexpected finding that this recombinant fragment binds to antibodies against *Bartonella henselae* in an IgG ELISA. The 15 amino acids at the C-terminal end confers the 17-kDa protein its ability to recognize the antibody in positive sera (See, FIG. 16).

Figure 14:
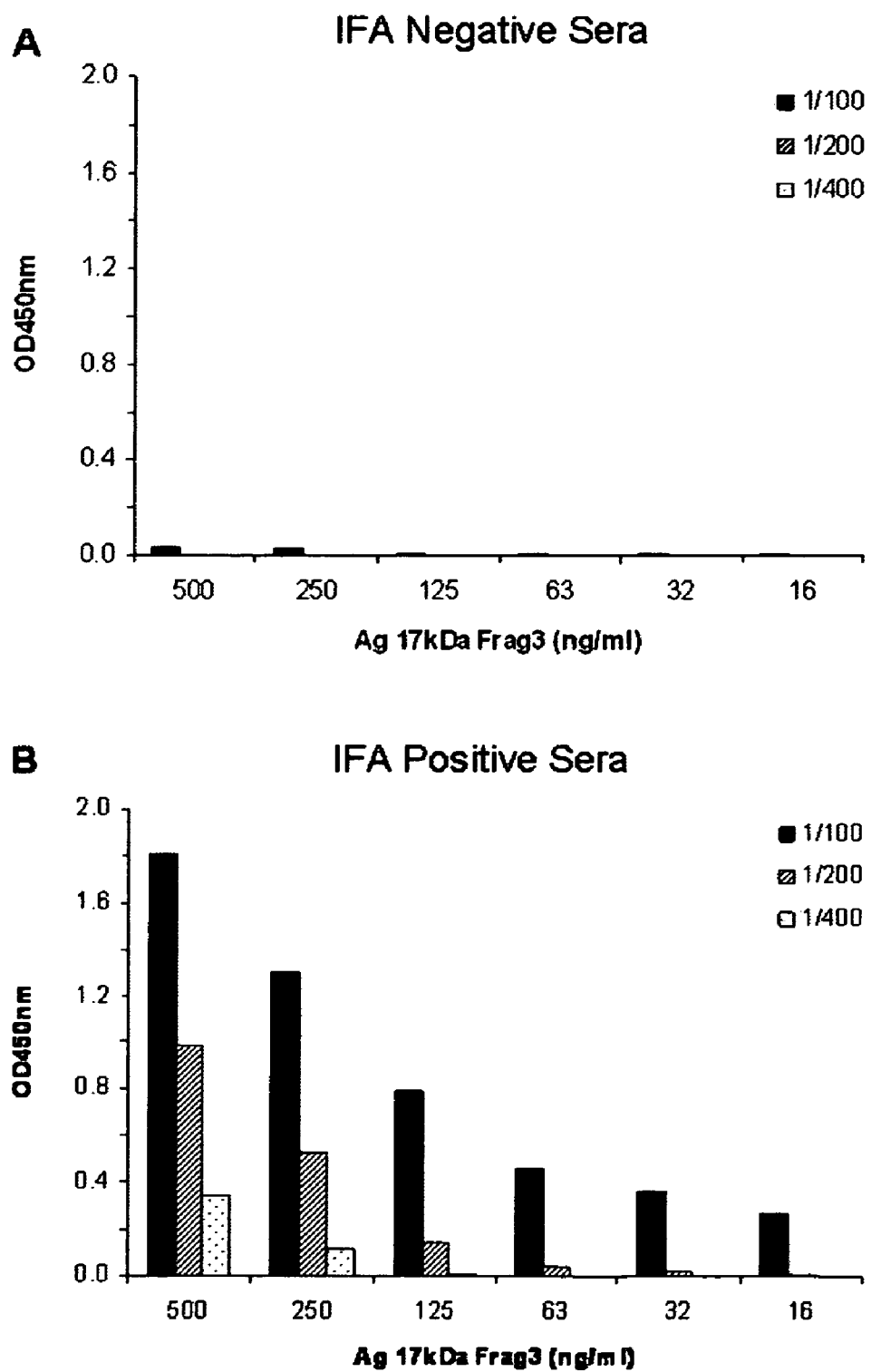
FIG. 14A is a graph of optical readout data for ELISA assays using recombinant Fragment 3 as coating antigen with IFA negative sera.
FIG. 14B is a graph of optical readout data for ELISA assays using recombinant Fragment 3 as coating antigen with IFA positive sera.
Figure 15:
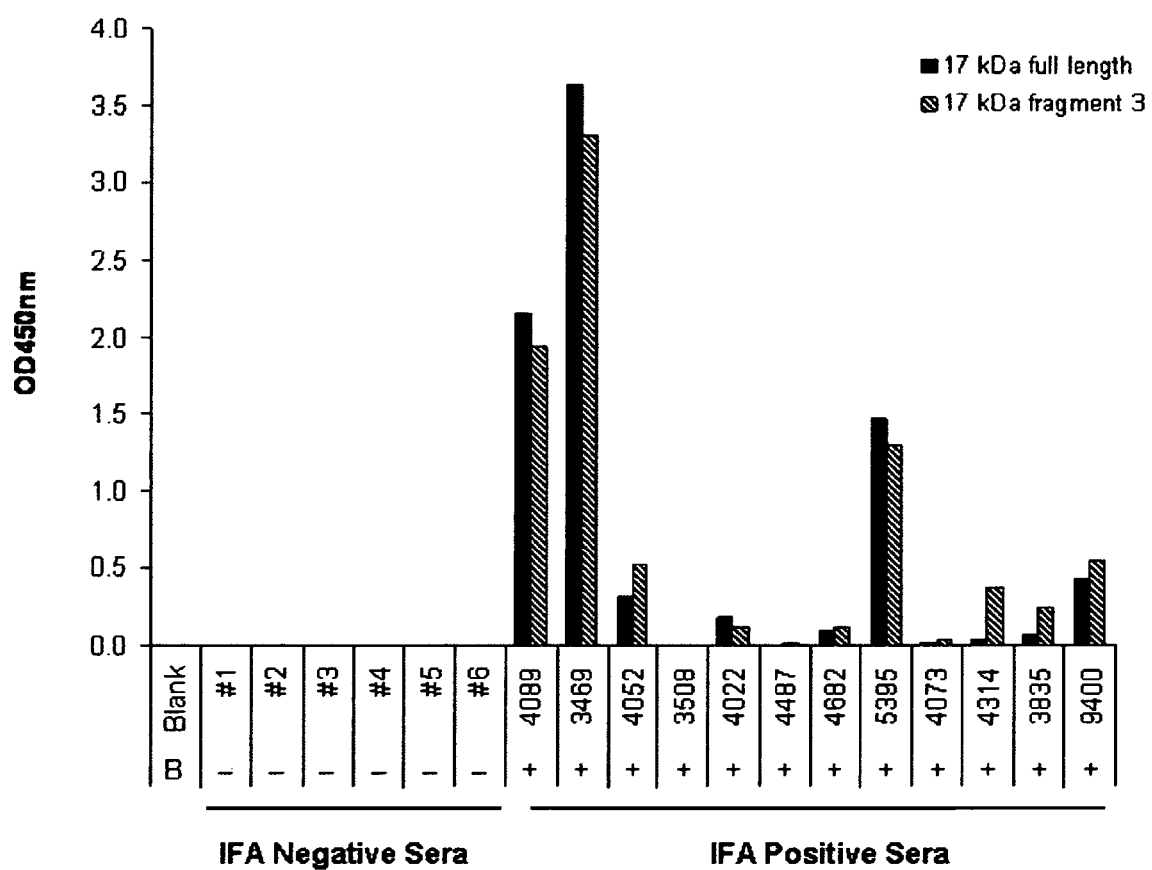
FIG. 15 is a graph of optical readout data for ELISA assays comparing recombinant Fragment 3 as coating antigen to full length 17-kDa protein in 12 IFA positive sera and 6 IFA negative sera.

FIGS. 14A and 14B present the results of the ELISA analysis for recombinant Fragment 3. A significant difference between IFA sero-positive sera and IFA-negative sera at coating concentration from 100 ng/ml to 16 ng/ml and a sera dilution of 1:100, while the difference diminished when sera was diluted 1:200 or above. The capacity of the recombinant protein to differentiate positive sera to negative sera was enhanced at higher coating concentrations from 16 ng/ml to 500 ng/ml. From this analysis, it was determined that 250 ng/ml coating antigen (recombinant Fragment 3) was sensitive enough to specifically identify antibodies.

Example 6

Comparison of Full-Length 17-kDa Protein to Recombinant Fragment 3 in the Detection of *Bartonella henselae*

It should be noted that the present recombinant Fragment 3 has a mutation at amino acid position 147 which is different than the wild-type 17-kDa (accession number: gi|49476013|ref|YP_034054.1|). Specifically, the present recombinant Fragment 3 has an amino acid substitution (i.e., glutamine) at that position while the wild-type 17-kDa has an amino acid of arginine (See, FIG. 22). Thus, the present recombinant Fragment 3 is a mutated recombinant fragment.

The present recombinant Fragment 3 exhibited identical, if not better, ability to bind antibodies when compared with the full-length 17-kDa protein.

In this series of studies, a panel containing 12 IFA positive serum samples and 6 IFA negative serum samples was evaluated by ELISA using the respective antigen as the coating antigen. FIG. 15 presents the results of this ELISA analysis. Neither antigen reacted with any of the IFA negative serum samples. In fact, recombinant Fragment 3 displayed better sensitivity in detecting positive serum than the full length antigen. No difference between 17-kDa full length and recombinant Fragment 3 was observed in the ability to detect high positive serum samples, but recombinant Fragment 3 demonstrated a higher sensitivity in identifying middle-low positive serum samples #4314 and #3835. Neither antigen bound antibody in sample #3508.

The ability of the recombinant Fragment 3 to detect antibodies with the same or higher specificity as the full length antigen is unexpected. These data suggest that no hindrance effects exist from domains other than Fragment 3. 17-kDa protein appears to have only one single domain that is sufficient for the antibody binding activity.

To further characterize the comparative abilities of recombinant Fragment 3 and the full length protein to bind antibodies to *Bartonella henselae*, a broader panel of 47 serum samples (27 IFA positive serum samples and 20 IFA negative serum samples) was analyzed by ELISA. The raw data was analyzed with ROC curve comparison in statistic software MedCalc. Performance analysis of ROC curve is shown in FIG. 20. The area under 17-kDa Fragment 3 ROC curve (AUC) is 0.897 (95% confidence interval, 0.773-0.966), which is higher than AUC of 17-kDa full length (0.853, CI 0.719-0.939), suggesting that recombinant Fragment 3 may be a better antigen for ELISA detection as compared to that of full-length 17-kDa.

Example 7

17 kDa Recombinant Fragment 3 Mutation Construction

We constructed mutants of Fragment 3 using QuickChange Site-Directed Mutagenesis Kit (Stratagene, CA). The Plasmid containing Fragment 3 purified from BL21 (DE3) *E. coli* was used as a PCR template for the site-directed mutagenesis studies. The mutant E(13)D was amplified using primers in table 4. These oligonucleotide primers were extended and amplified by PCR as follows: 16 cycles of denaturing at 95° C. for 30 seconds, annealing at 55° C. for 1 minute, and extending at 68° C. for 6 minutes and 30 seconds.

To remove the parental DNA template, each PCR reaction mixture was incubated with DpnI enzyme at 37° C. for one hour. The enzyme-treated product was then transformed into XL1-Blue *E. coli*.

Sequence confirmation of all mutant clones was done prior to transformation into BL21(DE3) *E. coli* for expression (See, FIG. 24).

TABLE 4

Primers for Generation of Polynucleotides Encoding Four (4) Recombinant Mutation Fragments of the 17-kDa Fragment 3 of *Bartonella henselae*

| 17-kDa Fragment 3 Mutation | Primers | Nucleotide sequences | SEQ ID NOs |
|---|---|---|---|
| E(13)D | Forward | 5'-GCAAGCCCTGCAAATAGACCTGACTCTTCTCC-3' | SEQ ID NO: 34 |
|  | Reverse | 5'-GGAGAAGAGTCAGGTCTATTTGCAGGGCTTGC-3' | SEQ ID NO: 35 |
| L(16)V | Forward | 5'-GAGCTGACTGTTCTCCAGGCACAGCTGC-3' | SEQ ID NO: 36 |
|  | Reverse/ | 5'-GCAGCTGTGCCTGGAGAACAGTCAGCTC-3' | SEQ ID NO: 37 |
| ΔQ(11) | Forward | 5'-GCAAGCCCTG_ATAGAGCTGACTCTTCTCC-3' | SEQ ID NO: 38 |
|  | Reverse | 5'-GGAGAAGAGTCAGCTCTATCAGGGCTTGC-3' | SEQ ID NO: 39 |
| +V(17-18) | Forward | 5'-CTGACTCTTCTCGTCCAGGCACAGCTGC-3' | SEQ ID NO: 40 |
|  | Reverse | 5'-GCAGCTGTGCCTGGACGAGAAGAGTCAG-3' | SEQ ID NO: 41 |

Example 8

Cloning, Expression, Purification, and Activity Study of 17-kDa Fragment 3 mutations We prepared four Fragment 3 mutants using site-directed mutagenesis approach. In brief, we introduced point mutations to the N-terminus of Fragment 3 by using specific primers containing the desired mutation in high fidelity PCR reaction. Each mutant clone was transformed into *E. coli* BL21 (DE3) for expression. The four mutants: (1) mutant E(13)D, aspartic acid at amino acid #13 was substituted by glutamic acid; (2) mutant L(16)V, valine at amino acid #16 was substituted by leucine; (3) mutant ΔQ(11), amino acid #11 (glutamine) from C-terminus was deleted; (4) mutant +V(17-18), an amino acid valine was inserted between amino acid #17 and amino acid #18 from N-terminus (See, FIG. 23).

Figure 25:
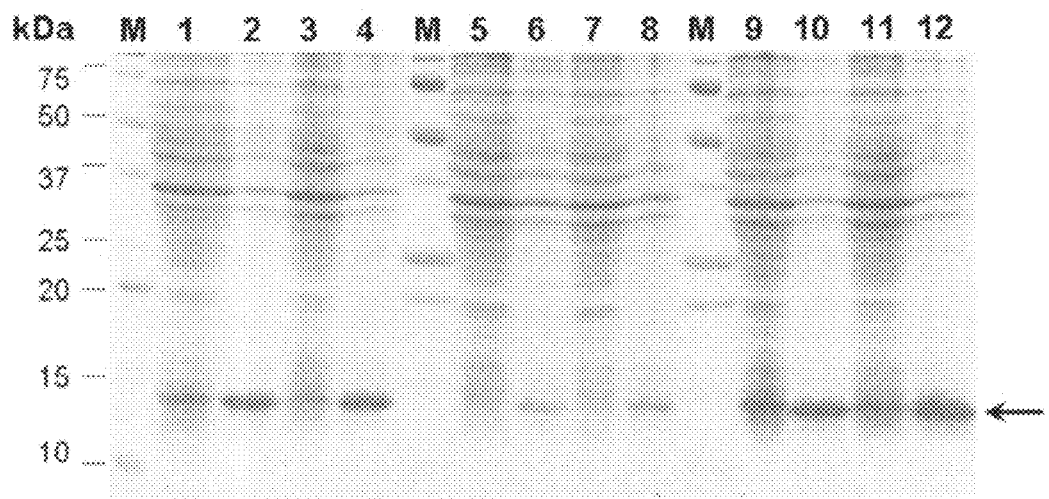
FIG. 25 is Coomassie blue-stained SDS electrophoresis gel showing induced expression of 17-kDa Fragment 3 various mutations in different transformed *E. coli* clones ((A) and (B)).
Figure 26:
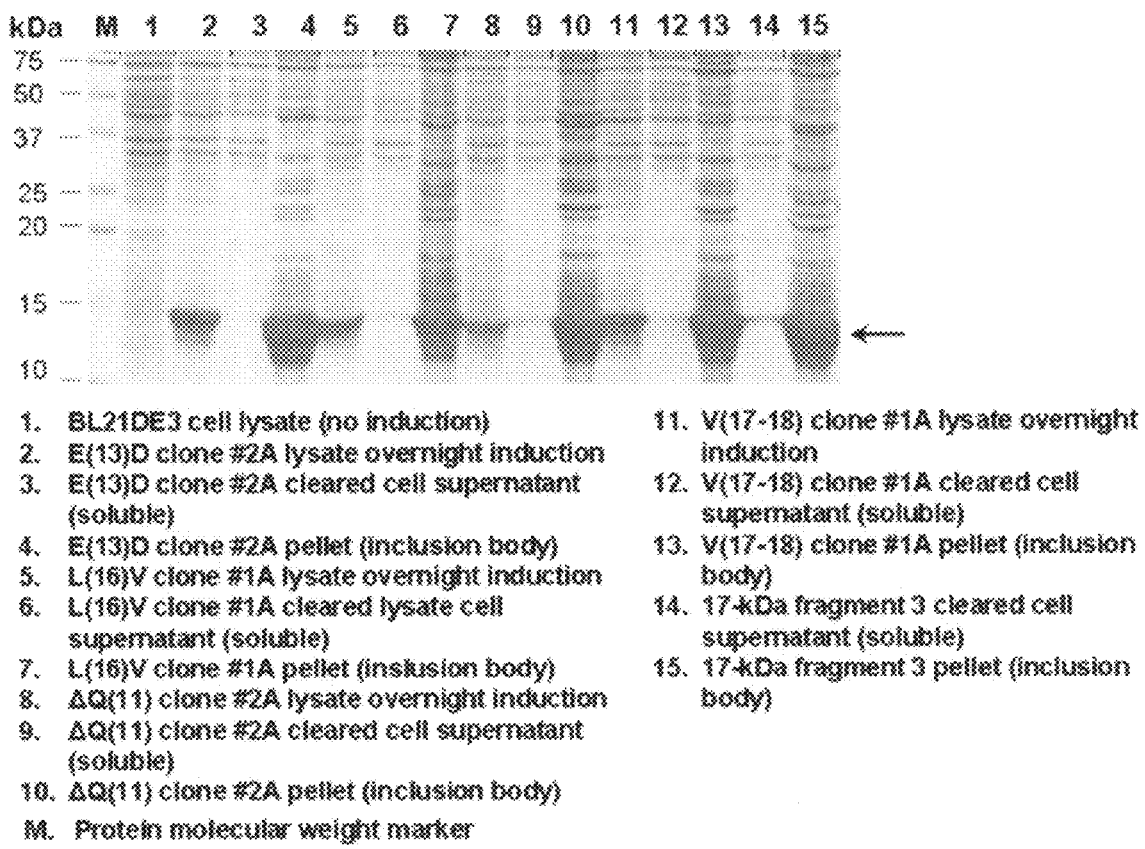
FIG. 26 is a Coomassie blue-stained SDS PAGE showing purification of 17-kDa Fragment 3 and mutation proteins (soluble vs. inclusion body).
Figure 27:
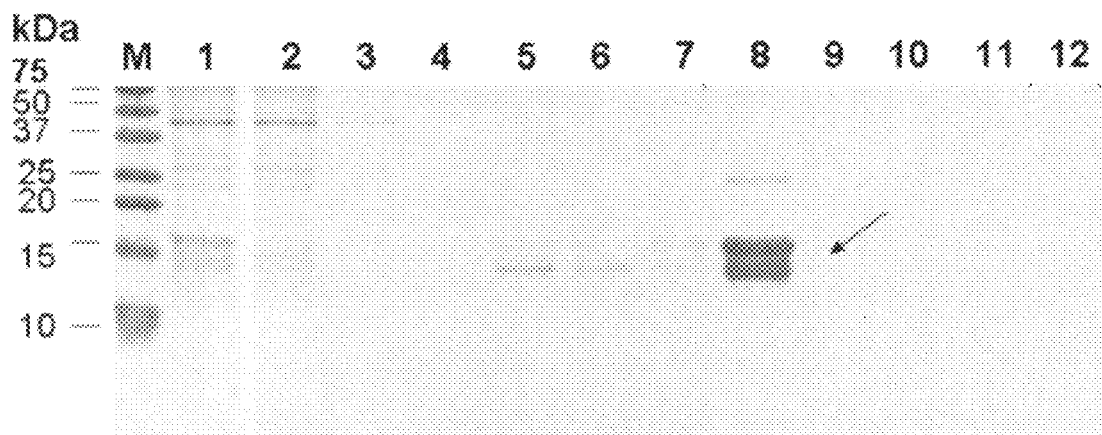
FIG. 27 is a Coomassie blue-stained SDS PAGE showing Ni-NTA purification of 17-kDa Fragment 3 conservative mutation E(13)D.
Figure 28:
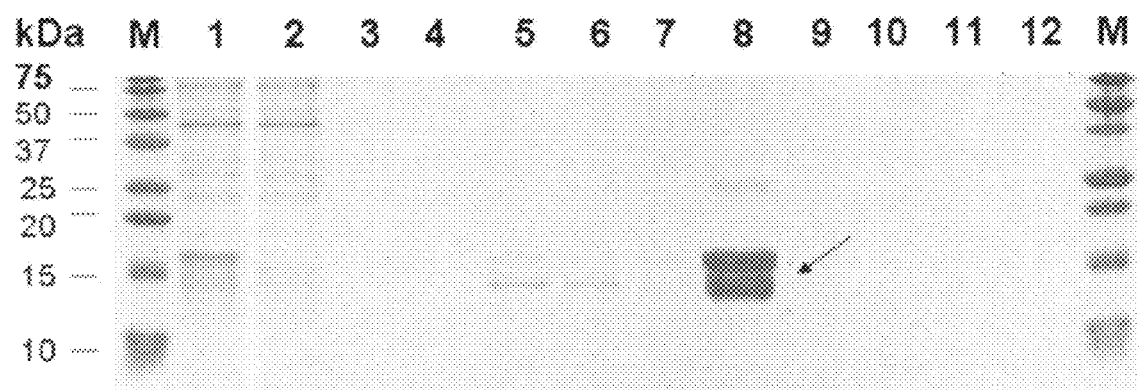
FIG. 28 is a Coomassie blue-stained SDS PAGE showing Ni-NTA purification of 17-kDa Fragment 3 conservative mutation L(16)V.
Figure 29:
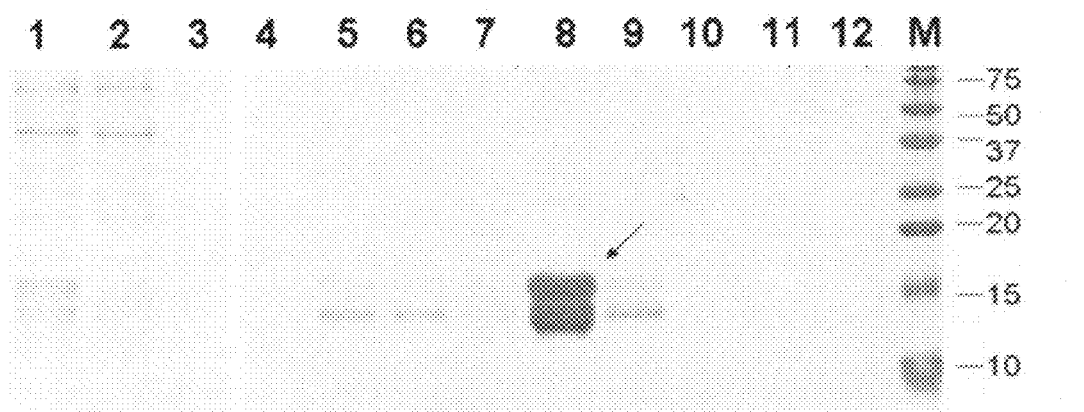
FIG. 29 is a Coomassie blue-stained SDS PAGE showing Ni-NTA purification of 17-kDa Fragment 3 deletion mutation ΔQ(11).
Figure 30:
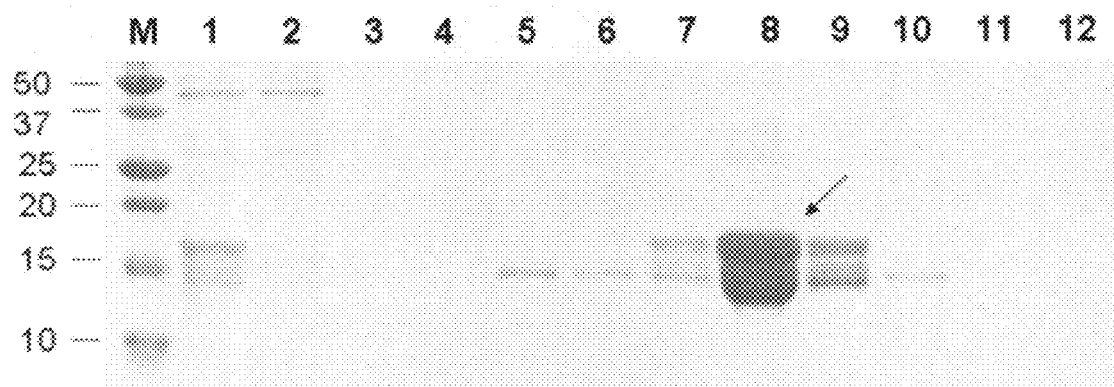
FIG. 30 is a Coomassie blue-stained SDS PAGE showing Ni-NTA purification of 17-kDa Fragment 3 insertion mutation +V(17-18).

All Fragment 3 mutants were successfully expressed in the Overnight Express Autoinduction System. The migration mass of Fragment 3 mutants were approximately 15-kDa as indicated in SDS PAGE. Among four mutants, conservative mutation E(13)D had the highest level of induction while deletion mutation ΔQ(11) had the lowest level of induction (See, FIG. 25). Similar to Fragment 3, mutants were all present within inclusion body post expression (See, FIG. 26). Therefore we purified mutants using nickel chelating affinity chromatography under denaturing conditions (8M urea), the same method as used for Fragment 3 (See, FIGS. 27, 28, 29, and 30).

Figure 31:
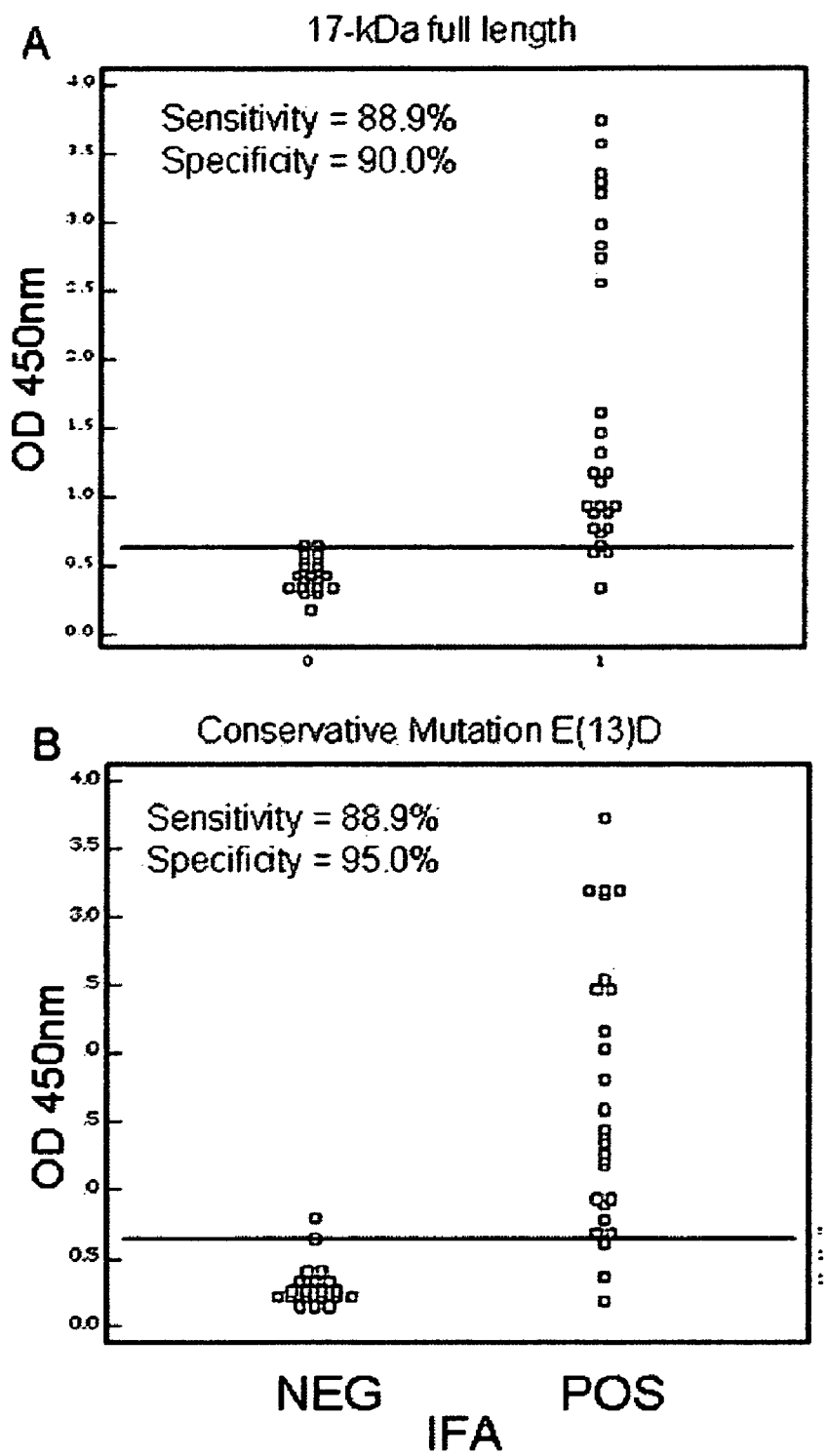
FIG. 31 depicts the dot plot illustrating the reactivity of each patient's sera towards 17-kDa polypeptides, 17-kDa Fragment 3 conservative mutations (immobilized) in an ELISA assay ((A) depicts the 17-kDa full length; (B) depicts conservative mutation E(13)D; (C) depicts conservative mutation L(16)V; and (D) depicts ROC for all three polypeptides).
Figure 31:
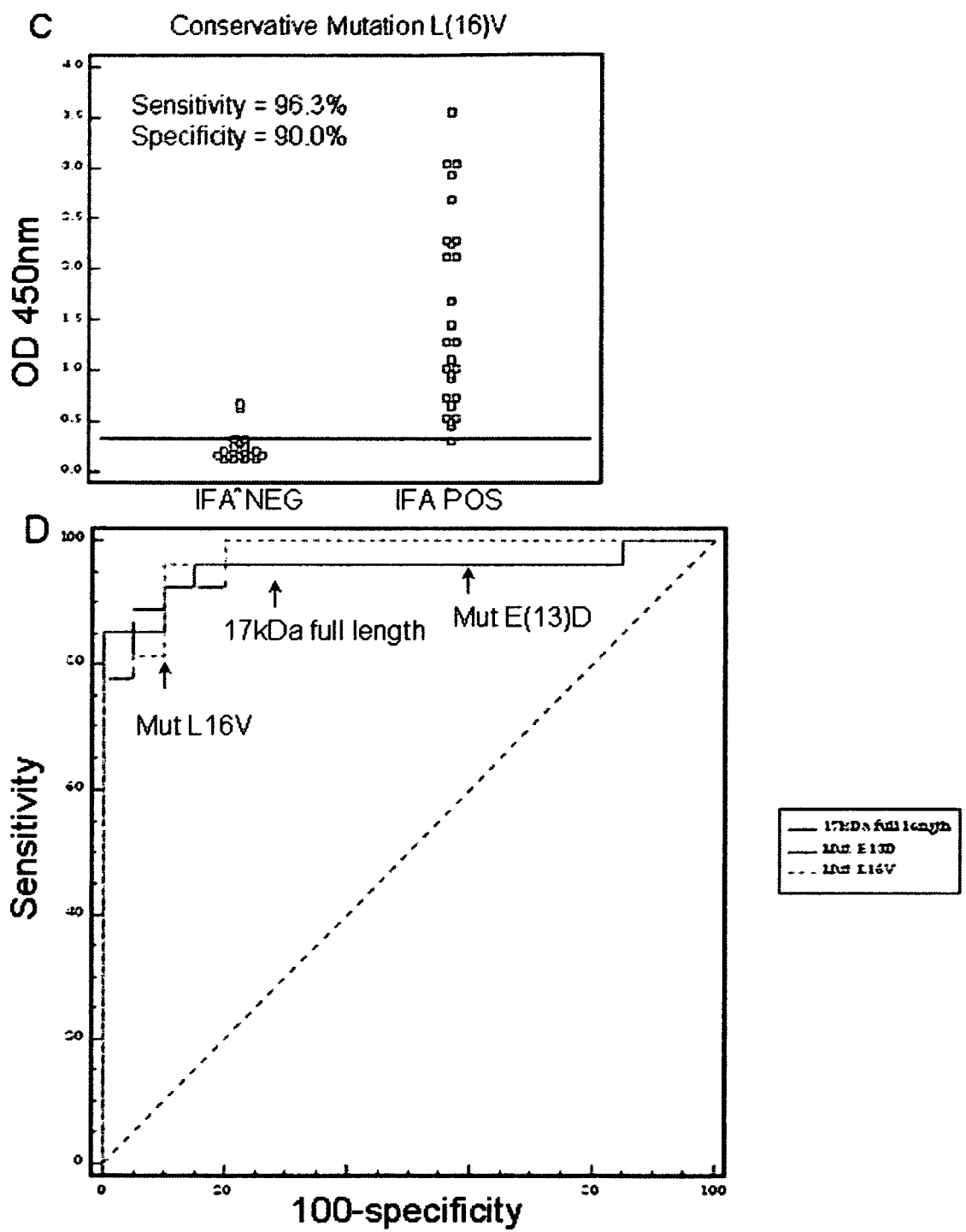
Figure 32:
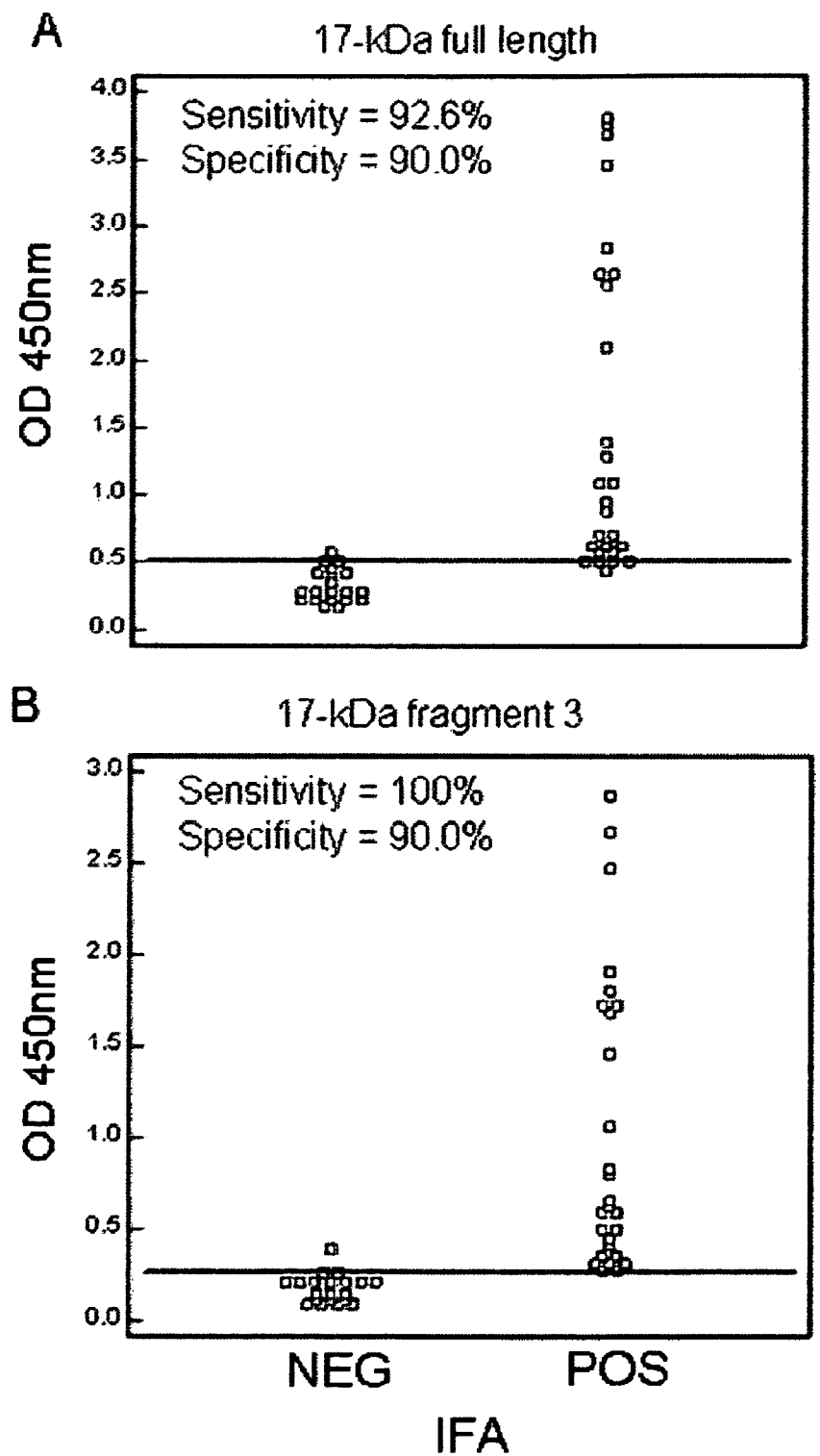
FIG. 32 depicts the dot plot illustrating the reactivity of each patient's sera towards 17-kDa polypeptides, 17-kDa Fragment 3, and deletion mutation (immobilized) in an ELISA assay ((A) depicts the 17-kDa full length; (B) depicts 17-kDa fragment 3; (C) depicts deletion mutation ΔQ(11); and (D) depicts ROC for all three polypeptides).
Figure 32:
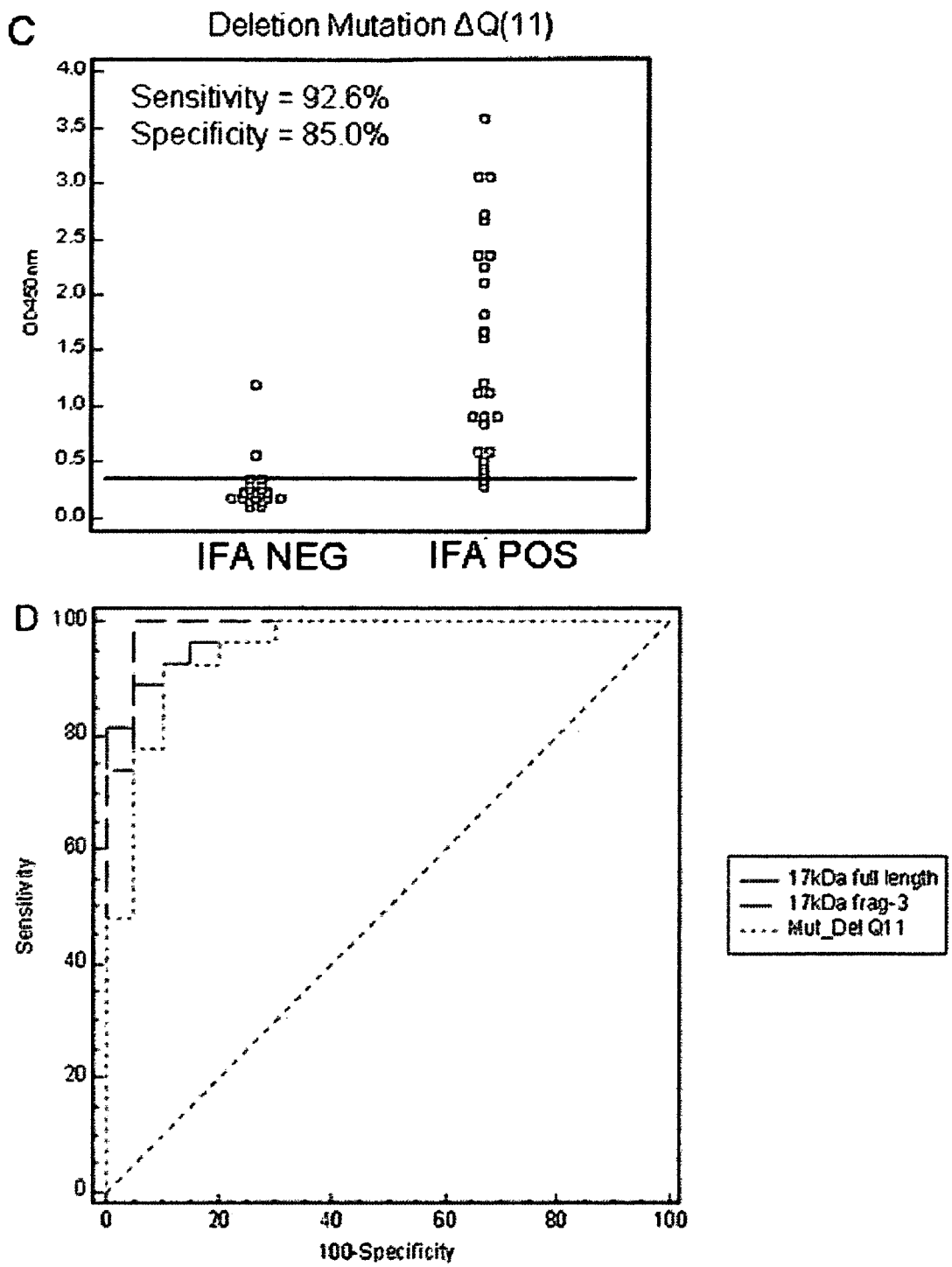

A panel of 47 human sera was used in an IgG ELISA to evaluate the sensitivity and specificity for Fragment 3 mutants. The raw data was analyzed by interactive dot diagram assay (FIGS. 31 and 32). Fragment 3 site-directed mutants, conservative mutations E(13)D and L(16)V, deletion mutation \Q(11), and insertion mutation +V(17-18), all had similar binding activity as compared to that of Fragment 3 (FIGS. 31, 32, and 33). No diminished antibody binding activity relative to Fragment 3 was observed in any of the N-terminus mutants.

Example 9

Synthetic Polypeptide Studies

Based on the data above, it is concluded that a single domain near the C-terminal of 17-kDa may possess an epitope sufficient for antibody binding. To further investigate the precise domain location, a panel of synthetic peptides was generated overlapping the single domain region.

Polypeptides were designed based on a prediction of relative antigenicity. Six (6) synthetic polypeptides were initially prepared (Table 5 and FIG. 16).

Using an ELISA assay, we tested the six (6) synthetic polypeptides and found that peptide 3C possesses the antibody binding activity. None of the other synthetic polypeptides had any activity. These data suggest the amino acid sequence of peptide 3C (i.e., SEQ ID NO: 22; EDLQKQLKEKLEKSDVRL) is necessary and sufficient for antibody binding.

TABLE 5

Five (5) Synthetic Polypeptides Directed to Fragment 3 of 17-kDa Protein

| Synthetic Polypeptides | Peptide Sequence | Length |
|---|---|---|
| Peptide 1 | ISHAKAQTATLTDEYYKK (SEQ ID NO: 19) | 18 aa |
| Peptide 3A | EQLQALQIELTLLQAQLQ (SEQ ID NO: 20) | 18 aa |

TABLE 5-continued

Five (5) Synthetic Polypeptides Directed to Fragment 3 of 17-kDa Protein

| Synthetic Polypeptides | Peptide Sequence | Length |
|---|---|---|
| Peptide 3B | QAKDTKTKEELREEQTQK (SEQ ID NO: 21) | 18 aa |
| Peptide 3C | EDLQKQLKEKLEKSDVRL (SEQ ID NO: 22) | 18 aa |
| Peptide 3D | EEQTQKKHEDLQKQLK (SEQ ID NO: 23) | 16 aa |
| Peptide 3E | EKLEKSDVRL (SEQ ID NO: 33) | 10 aa |

Figure 19:
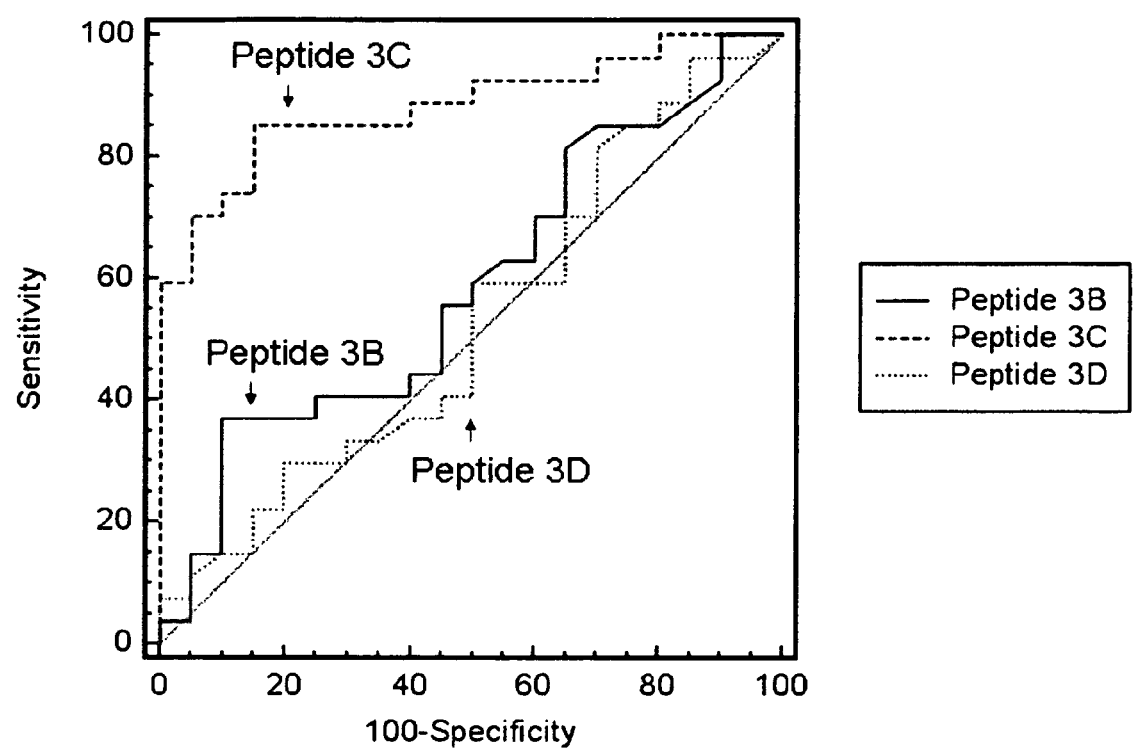
FIG. 19 is a Receiver Operator Characteristic Curve Comparison (ROC) of synthetic polypeptides 3B, 3C and 3D.
Figure 20:
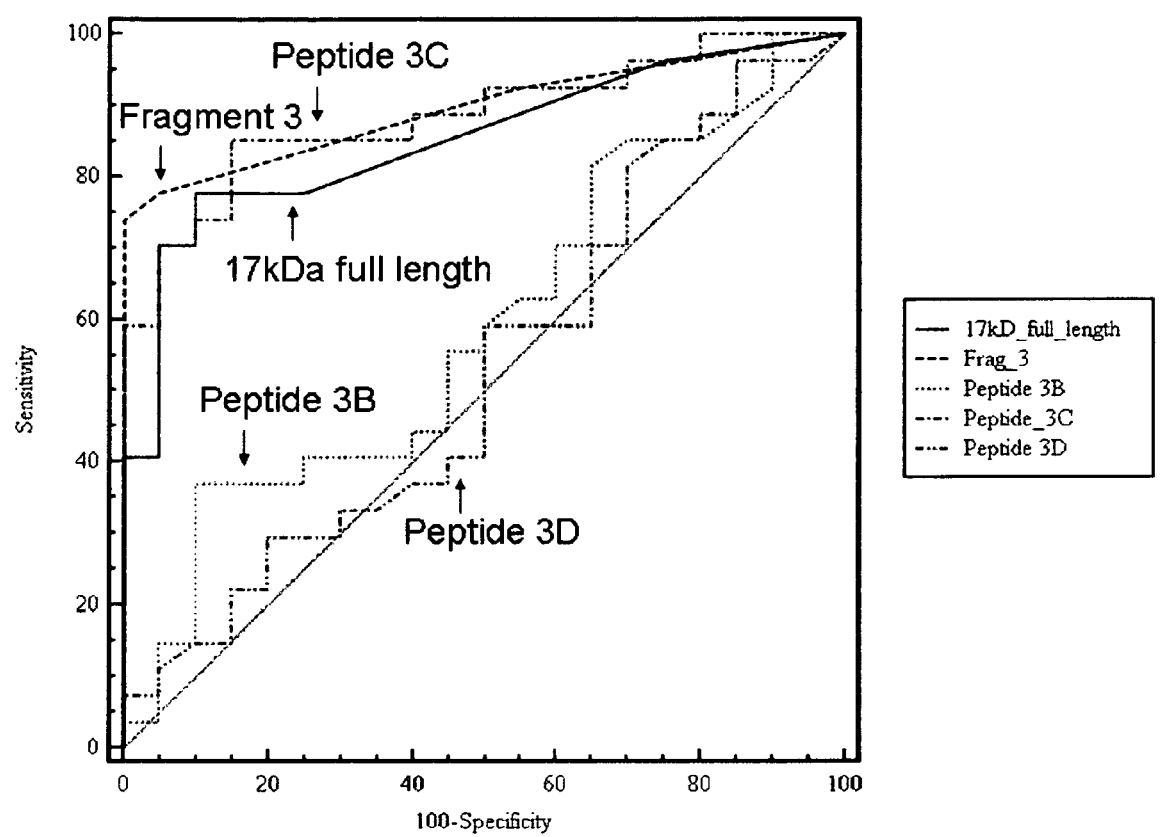
FIG. 20 is a Receiver Operator Characteristic Curve Comparison (ROC) of full-length 17-kDa, recombinant Fragment 3, synthetic peptides 3B, 3C and 3D.
Figure 21:
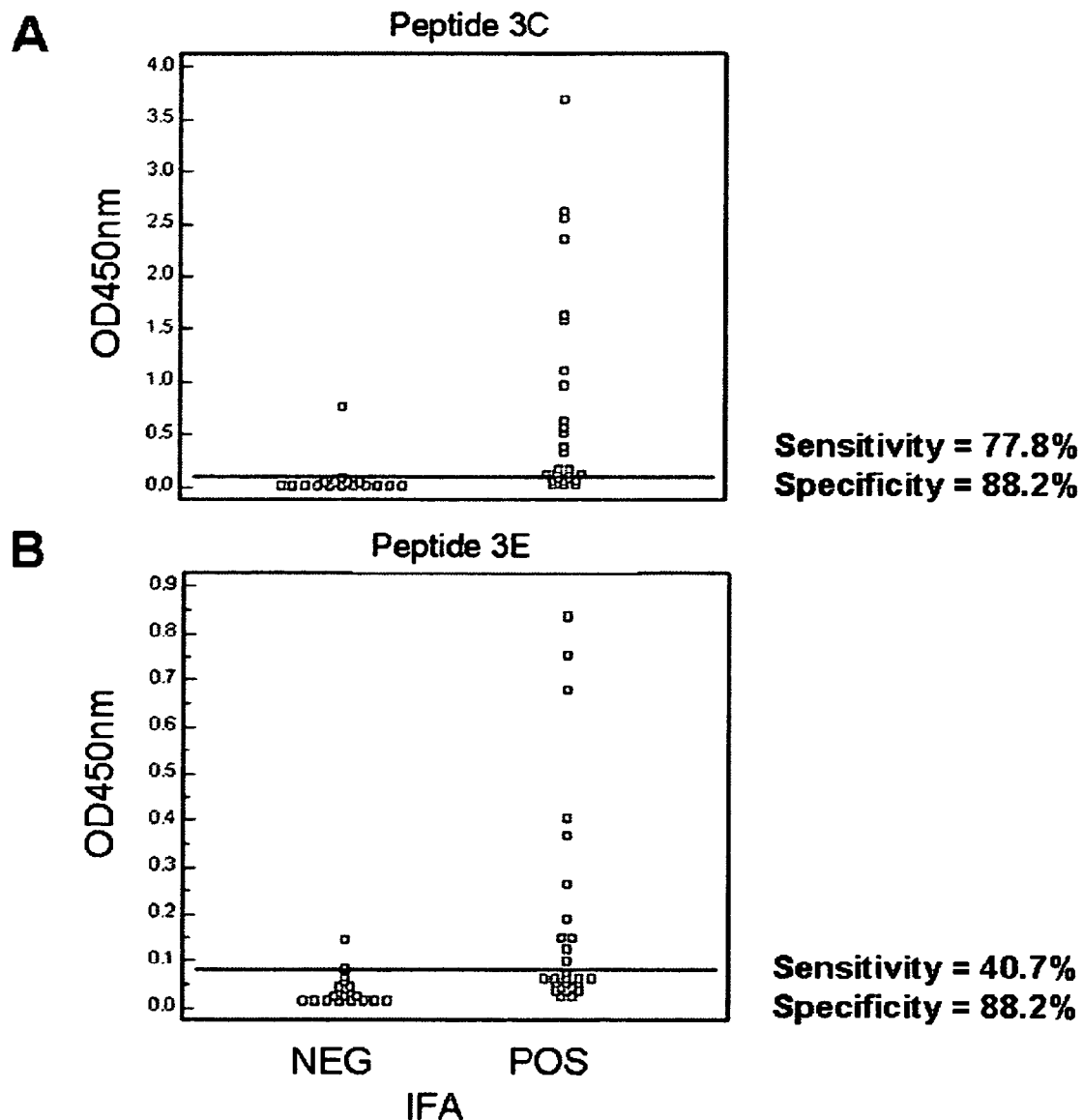
FIG. 21 depicts a dot plot illustrating the reactivity of each patient's sera towards synthetic polypeptide Peptide 3C (A) and Peptide 3E (B).
Figure 24:
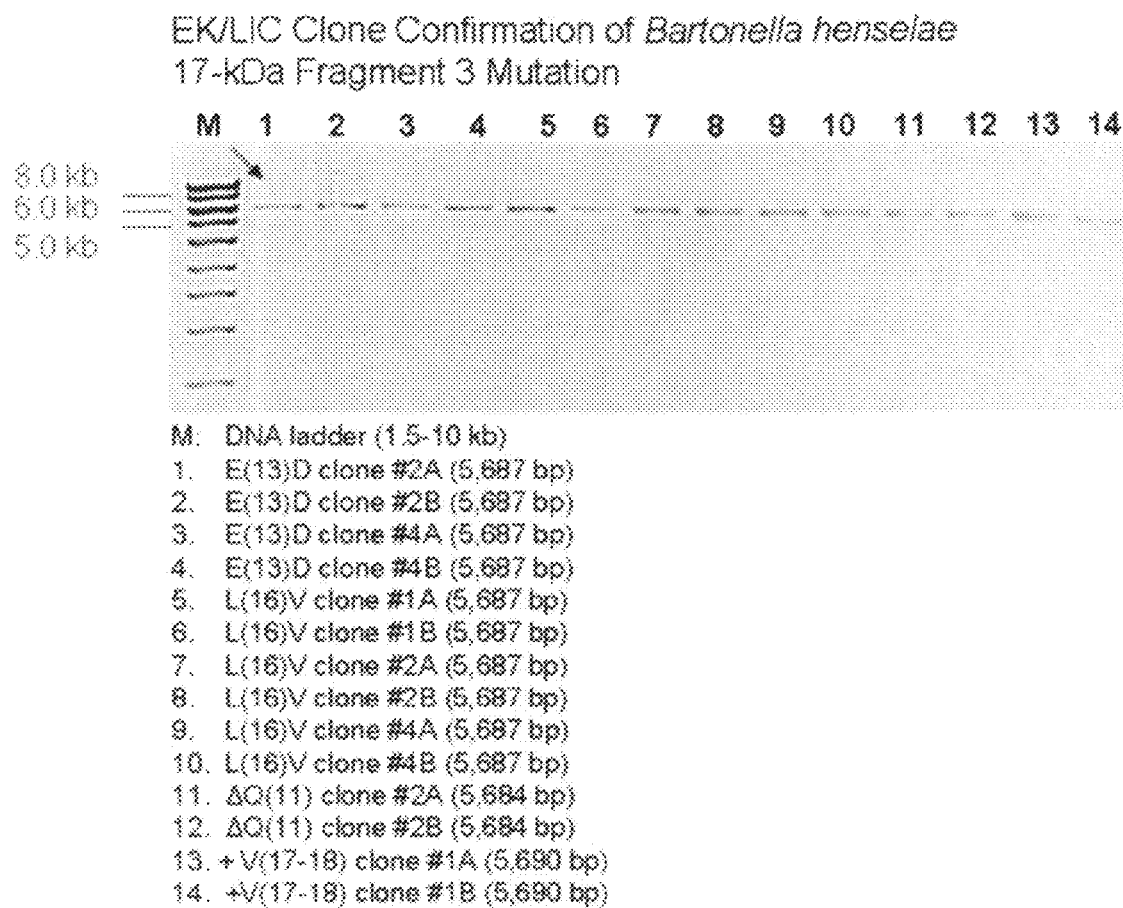
FIG. 24 is an agarose gel of the 17-kDa Fragment 3 mutation clone plasmids linearized by Kpn I restrict enzyme.

A panel of 47 human sera, including 27 IFA positive and 20 WA negative sera, was used. ROC analysis was used to analysis the binding activity via $OD_{450nm}$ (FIGS. 19 and 21). ELISA activity of synthetic peptides were summarized in Table 6. AUCs for peptide 3C, 3B, 3D, and 3E were 0.9, 0.5, 0.5, and 0.8 respectively (FIGS. 19 and 21). Because peptide 3C has a much higher AUC value (P<0.001), this peptide is interpreted to possess higher sensitivity and specificity as compared to the peptides 3B, 3D and 3E. Thus, the antibody recognition site seems to be present on peptide 3C (but not peptides 3B and 3D). While peptide 3E (10 amino acids at C-terminus of Peptide 3C) is not sufficient to complete antibody binding.

TABLE 6

ELISA Activity of Synthetic Polypeptides

| Synthetic Polypeptides | Sensitivity | Specificity | AUC |
|---|---|---|---|
| Peptide 3A | N/A | N/A | N/A |
| Peptide 3B | 33.3% | 90.0% | 0.5 |
| Peptide 3C | 77.8% | 88.2% | 0.9 |
| Peptide 3D | 85.2% | 25.0% | 0.5 |
| Peptide 3E | 40.7% | 88.2% | 0.8 |

N/A: not available

Example 10

Amino Acid Modifications of Peptide 3C

After establishing the active region of the 17-kDa protein is resided on the C-terminus (i.e., containing SEQ ID NO: 22), studies were performed by modifying the amino acid residues and correlate with their binding activity towards antibodies present in sero-positive patients suffering from *Bartonella henselae*.

In this series of study, the amino acid composition of the active region on peptide 3C was modified. The peptide modification includes (i) conservative subst TABLE 7-continued Amino Acid Modification of Synthetic Peptides

| Peptide Name | Modifications | Sequence of Peptides | Peptide Length | Binding Activity |
|---|---|---|---|---|
| Peptide 3C-RD | AA Substitution of the entire 18 AA | LKLELELVQDSDKQEKRK (SEQ ID NO: 29) | 18 | – |
| Peptide 3C-Ext1 | Addition of 4 AA | QKKHEDLQKQLKEKLEKSDVRL (SEQ ID NO: 30) | 22 | +++ |
| Peptide 3C-Ext2 | Addition of 7 AA | EQTQKKHEDLQKQLKEKLEKSDVRL (SEQ ID NO: 31) | 25 | +++ |
| Peptide 3C-Del | Deletion | ED_QKQLKEKLEKSDVRL (SEQ ID NO: 32) | 17 | +++ |

AA: amino acid

Example 11

ELISA Evaluation of Amino Acid Modified Polypeptides

We adopted an IgG ELISA assay and evaluated the binding activity of the modified peptides towards IgG. The ELISA procedure involves: (i) coating 96-well micro-titer plates with modified peptides at varying concentrations (e.g., 0.2-5 µg/ml) at 4° C. overnight; (ii) adding 5% skim milk to block non-specific binding; (iii) adding patients' sera to allow formation of antibody-antigen complex; (iv) detecting the antibody-antigen complex. IFA sero-positive sera served as positive controls and IFA sero-negative sera served as negative controls. Detection of antibody-antigen complex was performed with the use of horseradish peroxidase.

Individual Patient Study:

As shown in FIG. 17*a*, peptide 3C exhibited a dose-dependent increase in binding towards sero-positive serum (i.e., patient #4463) as measured by $OD_{450}$. These data indicate that the amino acid sequence of peptide 3C is responsible for the specific recognition of antibodies that is present in IFA-sero positive sera. FIG. 17*b* summarizes the effects of a single amino acid substitution (i.e., E to D at N-terminus of peptide 3C). The modified peptide (3C-CS1) has identical binding activity as compared to that of peptide 3C (FIG. 17). Similarly, conservative substitutions at other positions had the same binding activity (i.e., L to I in 3C-CS2 and L to V in 3C-CS3) (Table 7). In sum, these data show that conservative substitution of amino acid sequence of peptide 3C does not alter its specific recognition of antibodies.

Modified peptide based on substitution of the eight (8) amino acids at the N-terminus of peptide 3C (3C-RD1) had the same binding activity as compared to that of peptide 3C. In contrast, bulk substitution of the ten (10) amino acids at the C-terminus of peptide 3C (3C-RD2) completed abrogated the binding activity. (Table 7). These data show that the C-terminus of peptide 3C is critical for immunogenic recognition of antibodies in sera from patients infected with *Bartonella henselae*. In particular, the data suggest the ten (10) amino acids of the C-terminus on peptide 3C are important (SEQ ID NO: 33). The specificity of these 10 amino acids is further illustrated when the entire length of peptide 3C is substituted with different amino acids (3C-RD); the modified 3C-RD peptide had no binding activity (Table 7).

Modified peptide based on addition of four (4) or seven (7) amino acids at the N-terminus of peptide 3C (3C-Ext1 and 3C-Ext2) had the same binding activity as compared to that of peptide 3C. (Table 5). These data are consistent with our hypothesis that the C-terminus of peptide 3C is the antibody recognition site. Provided that the minimal C-terminus structure on peptide 3C is present, addition of amino acids to the N-terminus end seems to be irrelevant.

Furthermore, single amino acid deletion of peptide 3C (3C-Del) did not alter the binding activity (Table 7).

In sum, peptide 3C is useful in detecting the presence of antibodies against *Bartonella henselae* in patient sera. The studies with amino acid modification show that the C-terminus of peptide 3C is critical for this activity.

Panel Study:

A panel of 47 human sera was used in an ELISA assay to evaluate the sensitivity and specificity for synthetic polypeptides of 17-kDa protein. This panel contains 27 IFA positive sera and 20 IFA negative sera. Synthetic polypeptides used include amino acid substitution (Peptide 3C-CS3), addition (Peptide 3C-Ext2), and deletion (Peptide 3C-Del). Antibody binding was reflected by $OD_{450nm}$, which was analyzed by Interactive dot diagram in statistic software MedCalc.

Peptides 3C-CS3, 3C-Ext2, 3C-Del all had identical binding activity as compared to that of peptide 3C (FIG. 18). The sensitivity was ~80% and specificity was ~90%. Peptides 3C-RD, 3C-RD2 fail to bind antibody in TA positive sera (FIG. 18). The sensitivity was ~11% and specificity was 0%. Thus, the amino acids #139 to #148 seem to be sufficient for antibody binding.

Example 12

IgM ELISA Evaluation of 17-kDa Polypeptides

For the IgM Capture assay, purified recombinant 17-kDa full-length protein (1 mg/ml) was biotinylated using the Sulfo-NHS Biotin kit (Pierce, Rockford Ill.). MaxiSorp 96 well plates (Nunc, Rochester N.Y.) were coated with anti-human IgM (KPL, Gaithersburg, Md.) at a concentration of 1 μg/ml in coating buffer (0.015 M $Na_2CO_3$, 0.035 M $NaHCO_3$ [pH 9.6]) and incubated overnight at 4° C. The plates were washed with PBS-Tween 20 and blocked with 1% bovine serum albumin (BSA) at room temperature. IgM positive and negative patient sera were used. The sera were diluted 1:100 in 1% BSA with 0.05% Tween 20, prior to being run in duplicate, and reacted with the plates for 1 hr at room temperature.

Biotinylated recombinant 17-kDa protein was added to the plates at 1 µg/ml in dilution buffer and incubated at room temperature for 1 h with shaking. Streptavidin-HRP (Southern Biotech, Birmingham Ala.) was used to detect the plates followed by development with 3,3',5,5'-Tetramethylbenzidine (TMB) (Moss, Pasadena, Md.) for 30 minutes. The reaction was stopped with 2M HCl and the absorbance at 450 nm was recorded after a period of 5-30 minutes.

The results showed that recombinant 17-kDa full-length protein of Bartonella henselae could bind to IgM IFA-positive (n=13) and IFA-negative (n=34) patient samples with sensitivity and specificity values of 100% and 97.1%, respectively. Receiver operating characteristic (ROC) curve analysis was used to evaluate the performance of the IgM Capture method. ROC plots can be used to compare all tests, even when tests have quite different cutoff values. The study of area under the curve (AUC), which evaluates the probabilities of (1-Specificity) and Sensitivity, is an important statistical feature of such curves (i.e., for samples with Sensitivity=Specificity=100%, AUC would be 1.0). ROC analysis of the calibrated slopes revealed an AUC of 0.998 (95% CI, 0.919-1.000).

Buffer Compositions and Experimental Protocols
(i) Bind buffer
0.5 M Sodium chloride
20 mM Tris-Cl
5 mM Imidazole;
Buffer pH adjusted to 7.9
(ii) Charge buffer
50 mM $NiSO_4$
(iii) Bind buffer with urea
0.5 M Sodium chloride
20 mM Tris-Cl
5 mM Imidazole
8 M urea;
Buffer pH adjusted to 7.9
(iv) Wash buffer with urea
0.5 M Sodium chloride
20 mM Tris-Cl
20 mM Imidazole
8 M urea;
Buffer pH adjusted to 7.9
(v) Elute buffer I with urea
0.5 M Sodium chloride
20 mM Tris-Cl
250 mM Imidazole
8 M urea;
Buffer pH adjusted to 7.9
(vi) Elution buffer II with urea (pH 5.9)
100 mM Phosphate buffer
10 mM Tris-Cl
8 M urea;
Buffer pH adjusted to 5.9
(vii) Elution buffer III with urea (pH 4.5)
100 mM Phosphate buffer
10 mM Tris-Cl
8 M urea;
Buffer pH adjusted to 4.5

Buffer Exchange and Refolding of Purified 17-kDa Fragment 3 Protein

Antigen protein is not stable in elution buffer with high concentration of urea and imidazole, so it is important to perform buffer exchange step right after protein purification. We also have to refold antigen back to its native structure to develop ELISA assay; this re-naturing process also requires buffer exchange. We carried out multi-step buffer exchange dialysis to remove denaturant: 17-kDa Fragment 3 protein in 1 ml elution buffer with urea was injected into dialysis cassette (molecular weight cut off is 7 kDa); the dialysis cassette was stir floated first in 400 ml dialysis buffer 1 (PBS, 6 M urea, pH 7.5) at 4° C. for 2 hours, secondly in 400 ml dialysis buffer 2 (PBS, 4 M urea, pH 7.5) at 4° C. for 2 hours, thirdly in 400 ml dialysis buffer 3 (PBS, 2 M urea, pH 7.5) at 4° C. for 2 hours, and finally in 400 ml dialysis buffer 4 (PBS, 1 M urea, pH 7.5) at 4° C. for 2 hours. Here we used 1 mol/L of urea to prevent antigen protein aggregation and/or destabilize improperly folder protein.

IgG ELISA Analysis

Purified protein was diluted in coating buffer to a final concentration 250 ng/ml. Antigen was adhered to 96-well plate by applying 100 µl above prepared solution per well and incubate at 4° C. for 18 hours. We removed uncoated antigen by washing plate three times with PBST wash buffer. After washing, post-coating was done with 300 µl blocking reagent General Blocker BB1 each well for 1 hour at 22° C. Then primary polyclonal antibody from 100 µl serum in 1:100 sample dilution buffer each well was allowed to react with coated antigen for 1 hour at 22° C. After five times washing with PBST wash buffer, we incubated each well with 100 µl peroxidase conjugated goat anti-human IgG (KPL, 1:20,000 from 1 mg/ml stock in sample dilute buffer) for 30 minutes at 22° C. The excess amount of secondary antibody was also removed by five times washing with PBST wash buffer. The reaction were visualized by adding 100 µl substrate 3,3'5,5'-Tetramethylbenzidine Solution and incubated at 22° C. for 15 minutes. In the end, we terminated reaction with 100 µl 0.5 M $H_2SO_4$ per well before taking $OD_{450nm}$ measurement. Receiver operating characteristic curve (ROC) analysis was calculated with associated 95% confidence interval using a binomial distribution with MedCalc program.

ELISA Buffer Compositions
(i) Coating buffer (pH 9.6)
0.015M $Na_2CO_3$
0.035M $NaHCO_3$
(ii) PBST wash buffer
Phosphate Buffered Saline
0.05% Tween-20
(iii) Sample dilution buffer
Phosphate Buffered Saline
1% BSA
0.05% Tween-20

Peptide Design

Recombinant fragments were designed with the use of % accessibility plot using the Protscale tool available at the Expasy website (www.EXPASY.org). Additional tools include antigenicity profile using the online tool available at CVC (Cancer Vaccine Center) Bioinformatics website (http://bio.dfci.harvard.edu/Tools/antigenic.html), using the method of Kolaskar and Tongaonkar (FEBS Lett. 1990 Dec. 10; 276(1-2):172-172) and hydrophobicity profile using the Protscale tool available at the Expasy website (www.EXPASY.org). For chemical synthetic peptide design, other analytic tool was employed. To predict potential antigenic regions of 17-kDa Fragment 3, Jameson and Wolf method (commercially available computer program) was adopted. In this method, the calculation is based on antigenic scale which makes use of physicochemical properties of amino acid residues and their frequencies of occurrences in experimentally known segmental epitopes.

The foregoing detailed description provides exemplary embodiments of the invention and includes the best mode for practicing the invention. The description and illustration of embodiments is intended only to provide examples of the invention and not to limit the scope of the invention, or its protection, in any manner.

References

ADELSON, M. E., Rao, R. V., Tilton, R. C., Cabets. K., Eskow, E., Fein, L., Occi, J. L., and Mordechai, E. (2004). "Prevalence of Borrelia burgdorferi, Bartonella spp., Babesia microti, and Anaplasma phagocytophila in Ixodes scapularis ticks collected in Northern New Jersey," J Clin Microbiol. June; 42(6):2799-801.

AGAN, B. K., Dolan, M. J. (2002). "Laboratory diagnosis of Bartonella infections," Clin Lab Med. 2002 December; 22(4):937-62.

AMEREIN, M. P., De Briel, D., Jaulhac, B., Meyer, P., Monteil, H., and Piemont, Y. (1996). "Diagnostic value of the indirect immunofluorescence assay in cat scratch disease with Bartonella henselae and Afipia felis antigens," Clin Diagn Lab Immunol. 1996 March; 3(2):200-4.

ANDERSON, B., Lu, E., Jones, D., Regnery, R. (1995). "Characterization of a 17-kilodalton antigen of Bartonella henselae reactive with sera from patients with cat scratch disease," J Clin Microbiol. 1995 September; 33(9):2358-65.

ARVAND, M., Wendt, C., Regnath, T., Ullrich, R., and Hahn, H. (1998). "Characterization of Bartonella henselae isolated from bacillary angiomatosis lesions in a human immunodeficiency virus-infected patient in Germany," Clin Infect Dis. 1998 June; 26(6):1296-9.

ASHARAF, M., and Letha, S. (2002). "Cutaneous bacillary angiomatosis," Indian J Pediatr. 2002 November; 69(11): 1003-5.

BASS, J. W., Vincent, J. M., and Person, D. A. (1997). "The expanding spectrum of Bartonella infections: II. Cat-scratch disease," Pediatr Infect Dis J. February; 16(2):163-79.

BERGMANS, A. M., Peeters, M. F., Schellekens, J. F., Vos, M. C., Sabbe, L. J., Ossewaarde, J. M., Verbakel, H., Hooft, H. J., and Schouls, L. M. (1997). "Pitfalls and fallacies of cat scratch disease serology: evaluation of Bartonella henselae-based indirect fluorescence assay and enzyme-linked immunoassay," J Clin Microbiol. 1997 August; 35(8):1931-7.

BIRTLES, R. J., Harrison, T. G., and Taylor, A. G. (1991). "The causative agent of bacillary angiomatosis," N Engl J. Med. 1991 Nov. 14; 325(20):1447-8.

BRANLEY, J., Wolfson, C., Waters, P., Gottlieb, T., and Bradbury, R. (1996). "Prevalence of Bartonella henselae bacteremia, the causative agent of cat scratch disease, in an Australian cat population," Pathology, August; 28(3):262-5.

CHOMEL, B. B. (1996). "Cat-scratch disease and bacillary angiomatosis," Rev Sci Tech. 1996 September; 15(3):1061-73. Review.

CHOMEL, B. B. (2000). "Cat-scratch disease," Rev Sci Tech. 2000 April; 19(1):136-50.

ESKOW, E., Rao, R. V., and Mordechai, E. (2001). "Concurrent infection of the central nervous system by Borrelia burgdorferi and Bartonella henselae: evidence for a novel tick-borne disease complex," Arch Neurol. 2001 September; 58(9):1357-63.

FOURNIER, P. E., Mainardi, J. L., and Raoult, D. (2002). "Value of microimmunofluorescence for diagnosis and follow-up of Bartonella endocarditis," Clin Diagn Lab Immunol. 2002 July; 9(4):795-801.

LA SCOLA, B., and Raoult, D. (1999). "Culture of Bartonella quintana and Bartonella henselae from human samples: a 5-year experience (1993 to 1998)," Clin Microbiol. 1999 June; 37(6): 1899-905.

MARGILETH, A. M., and Baehren, D. F. (1998). "Chest-wall abscess due to cat-scratch disease (CSD) in an adult with antibodies to Bartonella clarridgeiae: case report and review of the thoracopulmonary manifestations of CSD," Clin Infect Dis. 1998 August; 27(2):353-7. Review.

REGNERY, R. and Tappero, J. (1995). "Unraveling mysteries associated with cat-scratch disease, bacillary angiomatosis, and related syndromes," Emerg Infect Dis. 1995 January-March; 1(1):16-21.

SANDER, A., Berner, R., Ruess, M. (2001). "Serodiagnosis of cat scratch disease: response to Bartonella henselae in children and a review of diagnostic methods," Eur J Clin Microbiol Infect Dis. 2001 June; 20(6):392-401.

SHAMAEI-TOUSI, A., Cahill, R., and Frankel, G. (2004). "Interaction between protein subunits of the Type IV secretion system of Bartonella henselae," Journal of Bacteriology. 186(14):4796-4801.

What is claimed is:

1. A synthetic polypeptide consisting of the amino acid sequence SEQ ID NO: 22, whereby said synthetic polypeptide, when assayed in an ELISA assay, reacts to IFA sero-positive sera and does not react to IFA sero-negative sera from a patient infected with *Bartonella henselae*.

2. A synthetic polypeptide consisting of an amino acid sequence selected from the group consisting of SEQ ID NO: 24, SEQ ID NO: 25, SEQ ID NO: 26 and SEQ ID NO: 27, whereby said synthetic polypeptide, when assayed in an ELISA assay, reacts to IFA sero-positive sera and does not react to IFA sero-negative sera from a patient infected with *Bartonella henselae*.

3. A synthetic polypeptide consisting of the amino acid sequence SEQ ID NO: 32, whereby said synthetic polypeptide, when assayed in an ELISA assay, reacts to IFA sero-positive sera and does not react to IFA sero-negative sera from a patient infected with *Bartonella henselae*.

4. A synthetic polypeptide consisting of an amino acid sequence selected from the group consisting of SEQ ID NO: 30 and SEQ ID NO: 31, whereby said synthetic polypeptide, when assayed in an ELISA assay, reacts to IFA sero-positive sera and does not react to IFA sero-negative sera from a patient infected with *Bartonella henselae.*

5. A kit useful in the detection of *Bartonella henselae*, said kit comprising:
   (a) the synthetic polypeptide according to claim 1; and
   (b) an instruction for using said synthetic polypeptide in an ELISA assay.

6. A kit useful in the detection of *Bartonella henselae*, said kit comprising:
   (a) the synthetic polypeptide according to claim 2; and
   (b) an instruction for using said synthetic polypeptide in an ELISA assay.

7. A kit useful in the detection of *Bartonella henselae*, said kit comprising:
   (a) the synthetic polypeptide according to claim 3; and
   (b) an instruction for using said synthetic polypeptide in an ELISA assay.

8. A kit useful in the detection of *Bartonella henselae*, said kit comprising:
   (a) the synthetic polypeptide according to claim 4; and
   (b) an instruction for using said synthetic polypeptide in an ELISA assay.

9. A method for detection of *Bartonella henselae* in a biological sample from a mammal, comprising the steps of:
   (a) immobilizing a synthetic polypeptide to a solid support, wherein said synthetic polypeptide consisting of an amino acid sequence selected from the group consisting of SEQ ID NO: 22, SEQ ID NO: 24, SEQ ID NO: 25, SEQ ID NO: 26, SEQ ID NO: 27, SEQ ID NO: 30, SEQ ID NO: 31, and SEQ ID NO. 32;
   (b) adding a biological sample onto said support to permit antibodies present in said biological sample to bind to said immobilized synthetic polypeptide;
   (c) washing to remove any unbound antibodies; and
   (d) detecting bound antibodies, wherein the presence of said bound antibodies is indicative of infection of said mammal with *Bartonella hensela.*

10. The method according to claim 9, wherein said mammal is a human.

* * * * *